United States Patent
Yivgi-Ohana et al.

(10) Patent No.: US 10,702,556 B2
(45) Date of Patent: Jul. 7, 2020

(54) COMPOSITIONS AND METHODS FOR INDUCING ANGIOGENESIS

(71) Applicant: MINOVIA THERAPEUTICS LTD., Rehovot (IL)

(72) Inventors: Natalie Yivgi-Ohana, Haifa (IL); Uriel Halavee, Ramat Gan (IL); Shmuel Bukshpan, Ramat Hasharon (IL)

(73) Assignee: Minovia Therpautices Ltd., Rehovot (IL)

( * ) Notice: Subject to any disclaimer, the term of this patent is extended or adjusted under 35 U.S.C. 154(b) by 698 days.

(21) Appl. No.: 14/397,671

(22) PCT Filed: May 16, 2013

(86) PCT No.: PCT/IL2013/050423
§ 371 (c)(1),
(2) Date: Oct. 29, 2014

(87) PCT Pub. No.: WO2013/171752
PCT Pub. Date: Nov. 21, 2013

(65) Prior Publication Data
US 2015/0079193 A1 Mar. 19, 2015

Related U.S. Application Data

(60) Provisional application No. 61/647,546, filed on May 16, 2012, provisional application No. 61/778,671, filed on Mar. 13, 2013.

(51) Int. Cl.
A61K 35/50 (2015.01)
A61K 35/14 (2015.01)
(52) U.S. Cl.
CPC ............ *A61K 35/50* (2013.01); *A61K 35/14* (2013.01)
(58) Field of Classification Search
None
See application file for complete search history.

(56) References Cited

U.S. PATENT DOCUMENTS

| | | | |
|---|---|---|---|
| 7,279,326 B2 | 10/2007 | Weissig | |
| 7,339,090 B2 | 3/2008 | Christmann | |
| 7,407,800 B1 | 8/2008 | Benton | |
| 2005/0153381 A1 | 7/2005 | Marusich | |
| 2006/0024277 A1* | 2/2006 | Sivak | A61K 31/195 424/93.7 |
| 2010/0278790 A1 | 11/2010 | Prockop | |
| 2011/0008310 A1 | 1/2011 | Cataldo | |
| 2011/0105359 A1* | 5/2011 | Czerwinski | A01N 1/02 506/10 |
| 2012/0058091 A1 | 3/2012 | Rogers | |

FOREIGN PATENT DOCUMENTS

| | | |
|---|---|---|
| GB | 2350565 | 12/2000 |
| WO | 2004100773 | 11/2004 |
| WO | 2008137035 | 11/2008 |
| WO | 2008152640 | 12/2008 |
| WO | 2011059547 A2 | 5/2011 |
| WO | 2013/002880 A1 | 1/2013 |
| WO | 2013035101 | 3/2013 |
| WO | 2013/171752 A1 | 11/2013 |

OTHER PUBLICATIONS

Gasnier et al., (1993) Use of Percoll gradients for isolation of human placenta mitochondria suitable for investigating outer membrane proteins. Anal Biochem 212(1): 173-8 (6 pages).
Gavazza et al., (2005) Sensitivity of mitochondria isolated from liver and kidney of rat and bovine to lipid peroxidation: a comparative study of light emission and fatty acid profiles. Mol Cell Biochem 280(1-2): 77-82 (6 pages).
Griffiths and Rutter (2009) Mitochondrial calcium as a key regulator of mitochondrial ATP production in mammalian cells. Biochim Biophys Acta 1787(11): 1324-33 (10 pages).
Pipino et al., (2012) Placenta as a reservoir of stem cells: an underutilized resource? Br Med Bull, pp. 1-25 (25 pages).
Abramova et al., (1989) The functioning of mammalian mitochondria injected into fish embryos. Ontogenez 20(3): 320-3 abstract.
Baker et al., (2011) Use of the mouse aortic ring assay to study angiogenesis. Nat Protoc 7(1): 89-104.
Bourgeron et al., (1992) Isolation and characterization of mitochondria from human B lymphoblastoid cell lines. Biochem Biophys Res Comrnun 186(1): 16-23.
Brass et al., (2000) Multiple skeletal muscle mitochondrial DNA deletions in patients with unilateral peripheral arterial disease. Vasc Med 5(4): 225-30.
Choi et al., (2005) Analysis of proteome bound to D-loop region of mitochondrial DNA by DNA-linked affinity chromatography and reverse-phase liquid chromatography/tandem mass spectrometry. Ann N Y Acad Sci 1042: 88-100.
Clark and Shay (1982) Mitochondrial transformation of mammalian cells. Nature 295(5850): 605-7.
Csordás (2006) Mitochondrial transfer between eukaryotic animal cells and its physiologic role. Rejuvenation Res 9(4): 450-4.
Frazier et al., (2006) Mitochondrial morphology and distribution in mammalian cells. Biol Chem 387(12): 1551-8.
Frezza et al., (2007) Organelle isolation: functional mitochondria from mouse liver, muscle and cultured fibroblasts. Nat Protoc 2(2): 287-95.
Hartwig et al., (2009) A critical comparison between two classical and a kit-based method for mitochondria isolation. Proteomics 9(11): 3209-14.

(Continued)

*Primary Examiner* — Susan Hoffman
(74) *Attorney, Agent, or Firm* — DLA Piper LLP (US)

(57) ABSTRACT

The present invention relates to compositions and methods of inducing angiogenesis and methods of treating a pathology that would benefit from angiogenesis by use of a composition comprising partially purified intact mitochondria and/or ruptured mitochondria derived therefrom.

12 Claims, 23 Drawing Sheets

(56) References Cited

OTHER PUBLICATIONS

Katrangi et al., (2007) Xenogenic transfer of isolated murine mitochondria into human rho0 cells can improve respiratory function. Rejuvenation Res 10(4): 561-70.

Makris et al., (2007) Mitochondriopathy of peripheral arterial disease. Vascular 15(6): 336-43.

Martinez et al., (1997) Structural and functional changes in mitochondria associated with trophoblast differentiation: methods to isolate enriched preparations of syncytiotrophoblast mitochondria. Endocrinology 138(5): 2172-83.

Masuzawa et al., (2013) Transplantation of autologously derived mitochondria protects the heart from ischemia-reperfusion injury. Am J Physiol Heart Circ Physiol 304(7): H966-82.

McCully et al., (2009) Injection of isolated mitochondria during early reperfusion for cardioprotection. Am J Physiol Heart Circ Physiol 296(1): H94-H105.

Modica-Napolitano and Singh (2002) Mitochondria as targets for detection and treatment of cancer. Expert Rev Mol Med 4(9): 1-19.

Muftuoglu et al., (2003) Mitochondrial complex I and IV dysfunction of leukocytes in Parkinson's disease. Turk J Biochem 28(4): 246-251.

Murphy et al., (2008) Allogeneic endometrial regenerative cells: an "Off the shelf solution" for critical limb ischemia? J Transl Med 6: 45.

Parone et al., (2008) Preventing mitochondrial fission impairs mitochondrial function and leads to loss of mitochondrial DNA. PLoS One 3(9): e3257.

Piel et al., (2007) Mitochondrial resuscitation with exogenous cytochrome c in the septic heart. Crit Care Med 35(9): 2120-7.

Piel et al., (2008) Exogenous cytochrome C restores myocardial cytochrome oxidase activity into the late phase of sepsis. Shock 29(5): 612-6.

Pinkert et al., (1997) Mitochondria transfer into mouse ova by microinjection. Transgenic Res 6(6): 379-83.

Plotnikov et al., (2010) Cytoplasm and organelle transfer between mesenchymal multipotent stromal cells and renal tubular cells in co-culture. Exp Cell Res 316(15): 2447-55.

Rousou et al., (2004) Opening of mitochondrial KATP channels enhances cardioprotection through the modulation of mitochondrial matrix volume, calcium accumulation, and respiration. Am J Physiol Heart Circ Physiol 287(5): H1967-76.

Satoh et al., (2011) Mitochondrial damage-induced impairment of angiogenesis in the aging rat kidney. Lab Invest 91 (2): 190-202.

Schechner et al., (2003) Engraftment of a vascularized human skin equivalent. FASEB J 17(15): 2250-6.

Shi et al., (2008) Mitochondria transfer into fibroblasts: liposome-mediated transfer of labeled mitochondria into cultured cells. Ethnicity and Disease 18(S1): 43-44.

Spees et al., (2006) Mitochondrial transfer between cells can rescue aerobic respiration. Proc Natl Acad Sci U S A 103 (5):1283-8.

Szewczyk and Wojtczak (2002) Mitochondria as a pharmacological target. Pharmacol Rev 54(1): 101-27.

Takeda et al., (2005) Microinjection of cytoplasm or mitochondria derived from somatic cells affects parthenogenetic development of murine oocytes. Biol Reprod 72(6): 1397-404.

Tuckey and Sadleir (1999) The concentration of adrenodoxin reductase limits cytochrome p450scc activity in the human placenta. Eur J Biochem 263(2): 319-25.

Tuckey et al., (2005) Progesterone synthesis by the human placenta. Placenta 26(4): 273-81.

Wagle et al., (2011) The utility of an isolated mitochondrial fraction in the preparation of liposomes for the specific delivery of bioactives to mitochondria in live mammalian cells. Pharm Res 28(11): 2790-6.

Yamaguchi et al., (2007) Mitochondria frozen with trehalose retain a number of biological functions and preserve outer membrane integrity. Cell Death Differ 14(3): 616-24.

Yasuda et al., (2011) Tunneling nanotubes mediate rescue of prematurely senescent endothelial cells by endothelial progenitors: exchange of lysosomal pool. Aging (Albany NY) 3(6): 597-608.

Kuznetsov et al., (2003) Cryopreservation of mitochondria and mitochondrial function in cardiac and skeletal muscle fibers. Anal Biochem 319(2): 296-303 (8 pages).

Caicedo et al., (2015) MitoCeption as a new tool to assess the effects of mesenchymal stem/stromal cell mitochondria on cancer cell metabolism and function. Sci Rep 5: 9073; 10 pages.

Smith et al., (2004) Locally enhanced angiogenesis promotes transplanted cell survival. Tissue Eng 10(1-2): 63-71 (11 pages).

\* cited by examiner

Mito

Mito+Rotenone

Mito+Oligomycin

COMPOSITIONS AND METHODS FOR INDUCING ANGIOGENESIS

FIELD OF THE INVENTION

The present invention relates to compositions and methods of inducing angiogenesis and methods of treating a pathology that would benefit from angiogenesis by use of a composition comprising partially purified intact mitochondria and/or ruptured mitochondria derived therefrom.

BACKGROUND OF THE INVENTION

Mitochondria perform numerous essential tasks in the eukaryotic cell such as pyruvate oxidation, the Krebs cycle and metabolism of amino acids, fatty acids and steroids. The primary function of mitochondria is the generation of energy as adenosine triphosphate (ATP) by means of the electron-transport chain and the oxidative-phosphorylation system (the "respiratory chain"). Additional processes in which mitochondria are involved include heat production, storage of calcium ions, calcium signaling, programmed cell death (apoptosis) and cellular proliferation.

Mitochondria are found in all eukaryotes and vary in number and location depending on the cell type. Mitochondria contain their own DNA and their own machinery for synthesizing RNA and proteins. Mitochondrial DNA (mtDNA) has only 37 genes.

Eight to ten million Americans suffer from arterial occlusive disease, with approximately 500 to 1,000 new cases of chronic limb ischemia per million per year. Acute limb ischemia occurs when there is a lack of blood flow to a limb. It is usually due to either an embolism or thrombosis of an artery in those with underlying peripheral vascular disease. Patients with critical ischemia present with rest pain and/or with tissue loss, which can be ulceration, dry gangrene or wet gangrene, occurring in the lower extremities due to atherosclerotic occlusive disease of the iliac, femoral or popliteal arteries.

Peripheral artery disease (PAD) is a condition of the blood vessels that leads to narrowing and hardening of the arteries that supply the legs and feet. The narrowing of the blood vessels leads to decreased blood flow, which can injure nerves and other tissues.

Peripheral arterial disease is caused by arteriosclerosis, or "hardening of the arteries." This problem occurs when fatty material (plaque) builds up on the walls of arteries. This causes the arteries to become narrower. The walls of the arteries also become stiffer and cannot widen (dilate) to allow greater blood flow when needed. As a result, when the leg muscles work harder (such as during exercise or walking) they cannot get enough blood and oxygen. Eventually, there may not be enough blood and oxygen, even when the muscles are resting.

Critical limb ischemia (CLI) represents a syndrome that is associated with a particularly adverse natural history. Although clinicians increasingly recognize that peripheral arterial disease (PAD) includes a broad range of clinical syndromes, CLI is associated with very adverse short-term limb and systemic cardiovascular outcomes. CLI is not a specific disease per se; rather, it represents a syndrome that may develop from many fundamentally distinct pathophysiological processes, including advanced atherosclerosis, thromboembolism or atheroembolism, in situ thrombosis, and the arteritides, such as thromboangiitis obliterans (TAO, or Buerger's disease). Buerger's disease is manifested by recurring progressive inflammation and thrombosis (clotting) of small and medium arteries and veins of the hands and feet.

Myocardial infarction (MI), a major arterial occlusion disease, is a form of ischemic heart disease. MI is induced by interruption of blood supply to the heart, most commonly due to occlusion of a coronary artery. The resulting ischemia and ensuing oxygen deprivation, if left untreated for a sufficient period of time, may cause damage or death (infarction) of heart muscle tissue.

Clinical improvement and reduced need for amputation, has been reported, in CLI patients receiving autologous bone marrow or mobilized peripheral blood stem cells for stimulation of angiogenesis. While such treatments are currently being tested, practical and scientific pitfalls may limit widespread implementation if efficacy is proven. Hurdles to be overcome include: a) reduced angiogenic potential of autologous cells in aged patients with cardiovascular risk factors; b) adverse effects of bone marrow extraction and G-CSF mobilization; c) need for on-site cellular manipulation (Murphy M P. et al., (1998): Allogeneic endometrial regenerative cells: An "Off the shelf solution" for critical limb ischemia?); and d) risks in stem cell therapy such as inflammation as a result of immune-suppressive treatment, bleeding resulting from low level of platelets after treatment and development of malignancies.

United States Patent Publication No. 20110008310 discloses methods, kits, and compositions for mitochondrial replacement in the treatment of disorders arising from mitochondrial dysfunction.

International Publication No. WO 2013/035101 of the inventors of the present invention discloses compositions of functional mitochondria and uses thereof.

McCully et al. demonstrated injection of isolated mitochondria during early reperfusion for use in cardioprotection (McCully J. D. et al., 2009, Am J Physiol Heart Circ Physiol 296: H94-H105).

There still remains an unmet need for safe and efficient methods of inducing angiogenesis in general and for treating ischemia related diseases in particular.

SUMMARY OF THE INVENTION

The present invention provides compositions and methods for inducing angiogenesis in a tissue via administration of a composition comprising isolated or at least partially purified intact mitochondria and/or ruptured mitochondria produced therefrom. The invention further provides methods for treating a pathology which would benefit from angiogenesis and for enhancing engraftment of a tissue graft using the mitochondrial composition.

It is now disclosed that administration of the mitochondrial composition of the invention (i.e. compositions comprising isolated or at least partially purified intact mitochondria and/or ruptured mitochondria derived therefrom), to a tissue or a subject results in formation of new blood vessels. The formation of new blood vessels is beneficial in achieving improved blood flow, in assisting engraftment or in treatment of a pathology which would benefit from angiogenesis (e.g. ischemic vascular disease).

According to one aspect, the present invention provides a composition comprising partially purified intact mitochondria and/or ruptured mitochondria derived therefrom for use in inducing angiogenesis in a tissue; wherein said partially purified intact mitochondria have undergone at least one freeze-thaw cycle. According to some embodiments the mitochondria are obtained from placenta or from blood cells. Each possibility represents a separate embodiment of the present invention.

According to another aspect, the present invention provides a composition comprising ruptured mitochondria derived from partially purified intact mitochondria for use in inducing angiogenesis in a tissue. According to some embodiments, the ruptured mitochondria are derived from isolated intact mitochondria. According to some embodiments, the ruptured mitochondria are derived from partially purified intact mitochondria that have undergone at least one freeze-thaw cycle. According to other embodiments, the ruptured mitochondria are derived from partially purified intact mitochondria derived from placenta or blood cells.

According to another aspect, the present invention provides a composition comprising partially purified intact mitochondria and/or ruptured mitochondria derived therefrom for use in treating a subject afflicted with a pathology which would benefit from angiogenesis; wherein said partially purified intact mitochondria have undergone at least one freeze-thaw cycle. According to some embodiments, the present invention provides a composition comprising partially purified intact mitochondria and/or ruptured mitochondria derived therefrom for use in treating a tissue afflicted with a pathology which would benefit from angiogenesis. According to some embodiments, the present invention provides a composition comprising partially purified intact mitochondria and/or ruptured mitochondria derived therefrom for use in treating a tissue afflicted with a pathology which would benefit from angiogenesis, wherein the tissue is in a subject afflicted with a pathology which would benefit from angiogenesis.

According to some embodiments, the present invention provides a composition comprising ruptured mitochondria derived from partially purified intact mitochondria for use in treating a subject afflicted with a pathology which would benefit from angiogenesis.

According to another aspect, the present invention provides a composition comprising partially purified intact mitochondria and/or ruptured mitochondria derived therefrom for use in enhancing engraftment of a tissue graft; wherein said partially purified intact mitochondria have undergone at least one freeze-thaw cycle. Each possibility represents a separate embodiment of the present invention.

According to some embodiments, the present invention provides a composition comprising ruptured mitochondria derived from partially purified intact mitochondria for use in enhancing engraftment of a tissue graft.

As used herein, the term "partially purified mitochondria" refers to mitochondria separated from other cellular components, wherein the weight of the mitochondria constitutes between 20-80%, preferably 30-80%, most preferably 40-70% of the combined weight of the mitochondria and other sub-cellular fractions (as exemplified in: Hartwig et al., Proteomics, 2009, (9):3209-3214). Each possibility represents a separate embodiment of the present invention. According to another embodiment, partially purified mitochondria do not contain intact cells. According to some embodiments, the composition of the invention does not comprise intact cells.

As used herein, the term "isolated mitochondria" refers to mitochondria separated from other cellular components, wherein the weight of the mitochondria constitutes more than 80% of the combined weight of the mitochondria and other sub-cellular fractions.

According to some embodiments, the weight of the partially purified intact mitochondria and/or ruptured mitochondria derived therefrom constitutes between 20-80% of the combined weight of the mitochondria and other sub-cellular fractions in said composition. According to certain embodiments, the mitochondria of the invention are isolated mitochondria.

As used herein, the term "ruptured mitochondria" refers to mitochondria in which the inner and outer mitochondrial membranes have been sheared (torn) and/or perforated and/or punctured and the like. According to some embodiments, ruptured mitochondria were produced from partially purified or isolated intact mitochondria. According to some embodiments, ruptured mitochondria were produced from partially purified or isolated intact mitochondria that have undergone at least one freeze-thaw cycle. According to some embodiments, ruptured mitochondria were produced from partially purified or isolated intact mitochondria derived from a cell or tissue selected from the group consisting of: human placenta, human placental cell grown in culture and a human blood cell. Each possibility represents a separate embodiment of the present invention.

According to another aspect, the present invention provides a method of inducing angiogenesis in a tissue, the method comprising administering to the tissue a therapeutically effective amount of a composition comprising partially purified intact mitochondria and/or ruptured mitochondria derived therefrom; wherein said partially purified intact mitochondria have undergone at least one freeze-thaw cycle. Each possibility represents a separate embodiment of the present invention.

According to some embodiments, the present invention provides a method of inducing angiogenesis in a tissue, the method comprising administering to the tissue a therapeutically effective amount of a composition comprising ruptured mitochondria derived from partially purified intact mitochondria. According to another aspect, the present invention provides a method for treating a subject afflicted with a pathology which would benefit from angiogenesis, wherein the method comprises: providing a composition comprising partially purified intact and/or ruptured mitochondria derived therefrom, wherein said partially purified intact mitochondria have undergone at least one freeze-thaw cycle; and administering the composition to a tissue afflicted with a pathology which would benefit from angiogenesis. Each possibility represents a separate embodiment of the present invention.

According to some embodiments, the present invention provides a method for treating a subject afflicted with a pathology which would benefit from angiogenesis, the method comprises: providing a composition comprising ruptured mitochondria derived from partially purified intact mitochondria; and administering the composition to a tissue afflicted with a pathology which would benefit from angiogenesis. According to another aspect, the present invention provides a method for enhancing engraftment of a tissue graft, wherein the method comprises: providing a composition comprising partially purified intact mitochondria and/or ruptured mitochondria derived therefrom, wherein said partially purified intact mitochondria have undergone at least one freeze-thaw cycle; and administering the composition to a subject engrafted with the tissue graft. Each possibility represents a separate embodiment of the present invention.

According to some embodiments, the present invention provides a method for enhancing engraftment of a tissue graft, the method comprises: providing a composition comprising ruptured mitochondria derived from partially purified intact mitochondria; and administering the composition to a subject engrafted with the tissue graft.

According to some embodiments, the composition comprising the partially purified intact mitochondria further comprises a hypertonic solution. According to some embodiments, the hypertonic solution comprises a saccharide. According to some embodiments, the hypertonic solution comprises sucrose. According to some embodiments, the hypertonic composition comprises a saccharide at a concentration sufficient for preserving mitochondria intact. According to some embodiments, the hypertonic solution is the same type of buffer as an isolation buffer used to isolate the partially purified intact mitochondria. According to some embodiment, a hypertonic composition comprises a saccharide at a concentration of between 100 mM-400 mM, preferably between 100 mM-250 mM, most preferably between 200 mM-250 mM. Each possibility represents a separate embodiment of the present invention.

According to some embodiments, inducing angiogenesis in a tissue is inducing angiogenesis in an in-vivo tissue or an ex-vivo tissue. Each possibility represents a separate embodiment of the present invention.

According to another embodiment, the in-vivo tissue is selected from the group consisting of: an ischemic tissue, a tissue at risk of being affected with an ischemic damage, a tissue at risk of being affected by a vascular occlusion and a combination thereof. Each possibility represents a separate embodiment of the present invention.

According to another embodiment, the ex-vivo tissue is selected from the group consisting of: a tissue graft, a tissue grown in culture, an engineered tissue and a combination thereof. Each possibility represents a separate embodiment of the present invention.

According to another embodiment, inducing angiogenesis according to the invention is selected from the group consisting of: enhancing the level of blood perfusion, restoring blood flow, inducing blood flow, inducing growth of new blood vessels from pre-existing vessels, enhancing growth of new blood vessels from pre-existing vessels, inducing neovascularization and a combination thereof. Each possibility represents a separate embodiment of the present invention.

According to another embodiment, the in-vivo tissue is in a subject afflicted with a condition selected from the group consisting of: critical limb ischemia, peripheral artery disease, Buerger's disease, coronary heart disease, ischemic heart disease, myocardial infarction, traumatic brain injury, cerebrovascular accident and a combination thereof. Each possibility represents a separate embodiment of the present invention.

According to another embodiment, the pathology which would benefit from angiogenesis is selected from the group consisting of: critical limb ischemia, peripheral artery disease, Buerger's disease, coronary heart disease, ischemic heart disease, myocardial infarction, traumatic brain injury, cerebrovascular accident and a combination thereof. Each possibility represents a separate embodiment of the present invention.

According to another embodiment, a tissue afflicted with a pathology which would benefit from angiogenesis is a tissue at a site of narrowed arteries and/or hardened arteries and/or occluded arteries and a combination thereof. Each possibility represents a separate embodiment of the present invention.

According to another embodiment, the mitochondria of the invention are derived from a cell or a tissue selected from the group consisting of: placenta, placental cell grown in culture and a blood cell. Each possibility represents a separate embodiment of the present invention.

According to another embodiment, the mitochondria of the invention are derived from a cell or a tissue selected from the group consisting of: human placenta, human placental cell grown in culture and a human blood cell. Each possibility represents a separate embodiment of the present invention.

According to another embodiment, the mitochondrial composition further comprises a carrier. According to certain embodiments, the mitochondrial composition further comprises at least one bioactive agent.

According to another embodiment, the bioactive agent according to the invention is selected from the group consisting of: stem cell, growth factor, ion-exchange inhibitor, immunosuppressive drug, an antioxidant and a combination thereof. Each possibility represents a separate embodiment of the present invention.

According to alternative embodiments, the stem cell is selected from the group consisting of: neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts, neurons, oligodendrocytes, astrocytes, Schwann cells, skeletal muscle cells, cardiomyocytes, hepatocytes and a combination thereof. Each possibility represents a separate embodiment of the present invention.

According to another embodiment, the growth factor is Vascular Endothelial Growth Factor (VEGF), basic Fibroblast Growth Factor (bFGF) and a combination thereof. Each possibility represents a separate embodiment of the present invention.

According to another embodiment, the ion-exchange inhibitor is CGP37157.

According to another embodiment, the immunosuppressive drug is selected from the group consisting of: a glucocorticoid drug, a cytostatic agent, an alkylating agent, an anti-metabolite, methotrexate, azathioprine, mercaptopurine, a cytotoxic antibody, cyclosporin, tacrolimus, sirolimus, interferons, mycophenolate and a combination thereof. Each possibility represents a separate embodiment of the present invention.

According to another embodiment, the antioxidant is selected from the group consisting of: Vitamin A, Vitamin C, Vitamin E, Coenzyme Q10, N-acetylcysteine, Curcumin, Selenium, and a combination thereof. Each possibility represents a separate embodiment of the present invention.

According to another embodiment, the mitochondria of the invention have undergone at least one freeze-thaw cycle.

According to another embodiment, enhancing engraftment according to the method of the invention is enhancing engraftment of a graft selected from the group consisting of: a syngeneic graft, an allogeneic or a xenogeneic graft. Each possibility represents a separate embodiment of the present invention.

According to another embodiment, the tissue graft according to the invention is selected from the group consisting of: a skin graft, a vascular graft, a bone graft, a corneal graft, a ligament graft and an engineered graft. Each possibility represents a separate embodiment of the present invention.

According to another embodiment, enhancing engraftment according to the invention comprises at least one effect selected from the group consisting of: inducing angiogenesis in the tissue graft, restoring blood flow to the tissue graft, preventing rejection of the tissue graft, accelerating engraftment of the tissue graft and a combination thereof. Each possibility represents a separate embodiment of the present invention.

According to another embodiment, administration according to the invention is by a route selected from the group consisting of: intravenously, intra-arterially, administering into a blood-vessel wall, intramuscularly, intraperitoneally, transdermally, intradermally, intravitreally, subcutaneously and a combination thereof. Each possibility represents a separate embodiment of the present invention.

According to another embodiment, the tissue afflicted with a pathology which would benefit from angiogenesis is an ex-vivo tissue or an in-vivo tissue. Each possibility represents a separate embodiment of the present invention. According to another embodiment, the tissue is afflicted with a pathology which would benefit from angiogenesis.

According to another embodiment, administration of the composition to a subject engrafted with the tissue graft is by a route selected from the group consisting of: injecting into the tissue graft, injecting into a site of engraftment, administering topically to the tissue graft, administering topically to the site of engraftment and a combination thereof.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
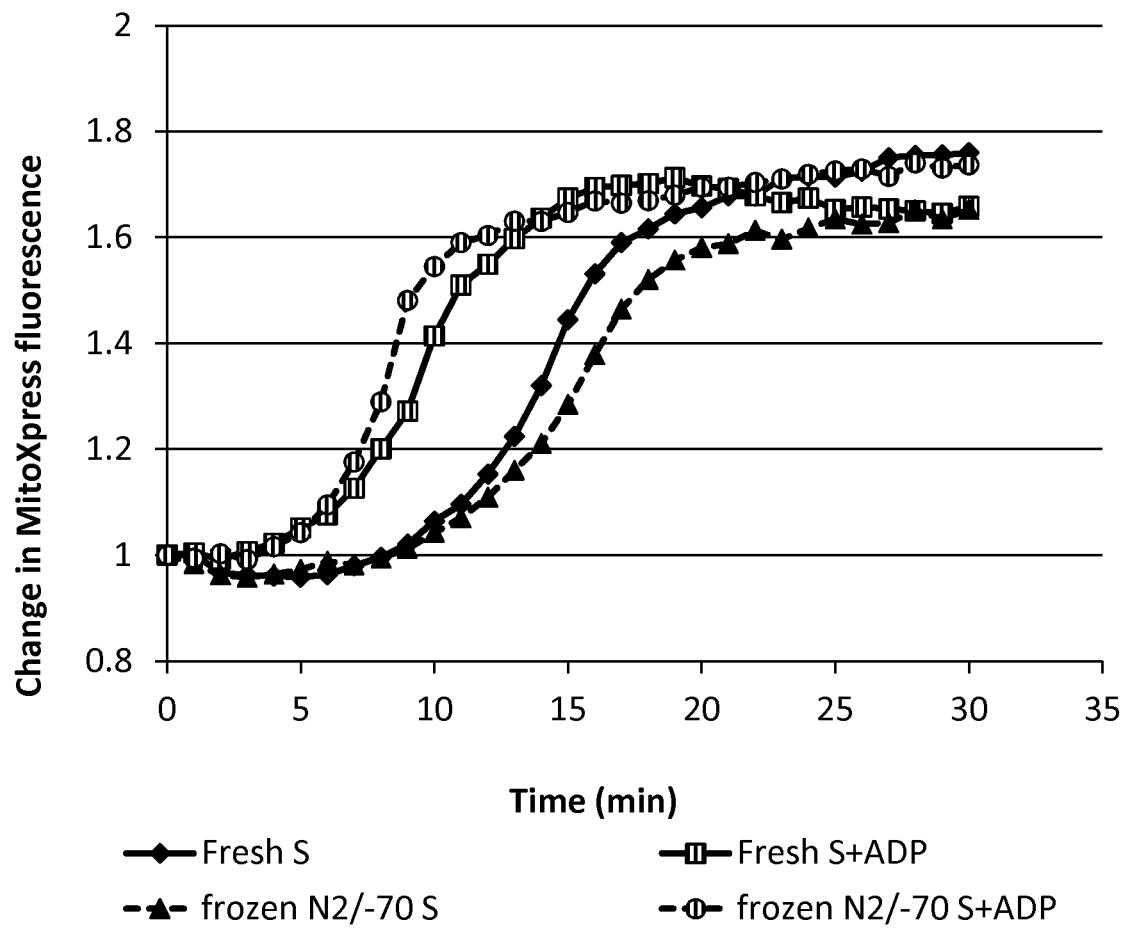
FIG. 1 is a dot-plot showing $O_2$ consumption over time in fresh ("Fresh") vs. frozen mitochondria ("N2/−70", flash frozen in liquid nitrogen and kept at −70° C. for 30 minutes). S=presence of 25 mM Succinate, S+ADP=presence of 25 mM Succinate and 1.65 mM ADP.

According to one aspect, the present invention provides a method for inducing angiogenesis in a tissue, comprising administering to the tissue a therapeutically effective amount of a composition comprising partially purified intact mitochondria and/or ruptured mitochondria derived therefrom; wherein said partially purified intact mitochondria have undergone at least one freeze-thaw cycle.

According to some embodiments, the present invention provides a method for inducing angiogenesis in a tissue, comprising administering to the tissue a therapeutically effective amount of a composition comprising ruptured mitochondria. According to some embodiments, the present invention provides a method for inducing angiogenesis in a tissue, comprising administering to the tissue a therapeutically effective amount of a composition comprising partially purified intact mitochondria; wherein said partially purified intact mitochondria have undergone at least one freeze-thaw cycle.

According to some embodiments, the present invention provides a method for inducing angiogenesis in a tissue, comprising administering to the tissue a therapeutically effective amount of a composition comprising mitochondria. According to some embodiments, the mitochondria are partially purified intact mitochondria. According to some embodiments, the mitochondria are partially purified, intact functional mitochondria. According to some embodiments, the mitochondria are ruptured mitochondria. According to some embodiments, the mitochondria are partially purified intact mitochondria that have undergone at least one freeze-thaw cycle. According to some embodiments, the mitochondria are intact mitochondria that have undergone at least one freeze-thaw cycle. As used herein, the terms "the composition", "the composition of the invention", "the mitochondria composition", "the mitochondrial composition" and "the mitochondria preparation" are used interchangeably.

According to some embodiments, the term "the composition of the invention", as used herein, refers to a composition comprising partially purified intact mitochondria and/or ruptured mitochondria derived therefrom. Each possibility represents a separate embodiment of the present invention. It is to be understood that the term "the composition of the invention" as used herein refers to a composition used with the methods of the present invention. According to some embodiments, the composition of the invention comprises partially purified intact mitochondria that have undergone at least one freeze-thaw cycle. According to some embodiments, the composition of the invention comprises ruptured mitochondria derived from partially purified intact mitochondria even without freezing and thawing. According to some embodiments, the composition of the invention comprises partially purified intact mitochondria that have undergone at least one freeze-thaw cycle and/or ruptured mitochondria derived therefrom. According to some embodiments, the composition of the invention comprises partially purified intact mitochondria derived from cells or tissue selected from the group consisting of: human placenta, human placental cells grown in culture and human blood cells. Each possibility represents a separate embodiment of the present invention. According to some embodiments, the composition of the invention comprises ruptured mitochondria derived from cells or tissue selected from the group consisting of: human placenta, human placental cells grown in culture and human blood cells. Each possibility represents a separate embodiment of the present invention. According to some embodiments, the composition of the invention comprises partially purified intact mitochondria and/or ruptured mitochondria derived therefrom, produced from cells or tissue selected from the group consisting of: human placenta, human placental cells grown in culture and human blood cells. Each possibility represents a separate embodiment of the present invention. It was previously known that intact isolated mitochondria provide cardioprotection during early reperfusion (McCully J. D. et al., 2009, Am J Physiol Heart Circ Physiol 296: H94-H105). That publication disclosed that injection of frozen thawed mitochondria to rabbit hearts failed to provide cardioprotection following induced ischemia. Similarly, results obtained with injection of mitochondrial components isolated by freeze-thaw failed to provide cardioprotection.

Unexpectedly, the present inventors have found that mitochondria that have undergone at least one freeze-thaw cycle are as functional as mitochondria that have not been frozen and thawed. Moreover, as exemplified below, the present invention have unexpectedly found that ruptured mitochondria are able to induce angiogenesis. The present invention provides a composition comprising ruptured mitochondria and/or partially purified intact mitochondria that have undergone at least one freeze-thaw cycle for treatment of heart pathologies related to ischemia such as, but not limited to, ischemic heart disease and myocardial infarction.

For non cardiac related conditions, it is to be noted that ruptured mitochondria and/or mitochondria that have been frozen and thawed and/or mitochondria that have not undergone at least one freeze-thaw cycle may be used for treatment of all those non-cardiac pathologies which would benefit from angiogenesis or for inducing angiogenesis according to the present invention.

According to some embodiments, the composition of the invention comprises ruptured mitochondria. According to some embodiments, the composition of the invention comprises partially purified intact mitochondria. According to other embodiments, the composition of the invention comprises partially purified intact mitochondria and ruptured mitochondria. According to some embodiments, the composition of the invention comprises ruptured mitochondria and at least one mitochondrial constituent released and/or secreted from the ruptured mitochondria. Each possibility represents a separate embodiment of the present invention. According to some embodiments, the composition of the invention comprises partially purified mitochondria. According to some embodiments, the composition of the invention comprises isolated mitochondria. According to some embodiments, the composition of the invention comprises a medium conditioned by mitochondria. According to other embodiments, the composition of the invention comprises at least one of the group consisting of: ruptured mitochondria, isolated mitochondria, partially purified mitochondria, partially purified intact mitochondria. As used herein, the term "medium conditioned by mitochondria" refers to a medium in which mitochondria were incubated and which contains mitochondrial constituents and/or elements secreted from mitochondria. According to some embodiments, the composition of the invention comprises partially purified functional mitochondria. According to some embodiments, the composition of the invention comprises partially purified mitochondria. According to some embodiments, the composition of the invention comprises isolated mitochondria. According to some embodiments, the composition of the invention comprises partially purified and/or isolated mitochondria. Each possibility represents a separate embodiment of the present invention. According to some embodiments, the composition of the invention comprises partially purified functional mitochondria and a saccharide in a concentration sufficient to preserve mitochondrial function; wherein the mitochondria are functional as measured by oxygen consumption.

According to some embodiments, the present invention provides method of inducing angiogenesis in a tissue, comprising administering to the tissue a therapeutically effective amount of a composition comprising partially purified functional mitochondria; wherein the composition comprises a saccharide in a concentration sufficient to preserve mitochondrial function and wherein the mitochondria are functional as measured by oxygen consumption.

As used herein, the terms "composition comprising partially purified intact mitochondria and/or ruptured mitochondria", "composition comprising partially purified intact mitochondria and/or ruptured mitochondria derived therefrom", "composition comprising mitochondria selected from the group consisting of: partially purified intact mitochondria and ruptured mitochondria", "composition comprising partially purified intact and/or ruptured mitochondria" and "composition comprising mitochondria" may interchangeably be used. The terms are directed to compositions which comprise partially purified intact mitochondria, ruptured mitochondria produced from partially purified intact mitochondria, or a combination thereof. According to some embodiments, the composition according to the present invention comprises ruptured mitochondria. Each possibility represents a separate embodiment of the present invention. Mitochondria include the mitochondrial genome which is a circular double-stranded molecule, consisting of 16,569 base pairs. It contains 37 genes including 13 protein-encoding genes, 22 transfer RNA (tRNA) genes and two ribosomal RNA (rRNA) genes. The 13 protein-encoding genes are components of the mitochondrial respiratory chain. The wild type (wt)-mtDNA molecule may also include sequence polymorphism, but it remains fully functional. Structurally, mitochondria range in diameter or width from 0.5 µm to 1 µm and have four compartments: the outer membrane, the inner membrane, the intermembrane space and the matrix.

As used herein, the terms "mitochondria" or "the mitochondria of the invention" are interchangeable and refer to partially purified intact mitochondria and/or ruptured mitochondria derived therefrom. According to some embodiments, the mitochondria of the invention are intact mitochondria. According to some embodiments, the mitochondria of the invention are partially purified intact mitochondria. According to some embodiments, the mitochondria of the invention are partially purified mitochondria. According to some embodiments, the composition of the invention comprised partially purified mitochondria and/or ruptured mitochondria produced from partially purified mitochondria. Each possibility represents a separate embodiment of the present invention.

As used herein, the term "partially purified intact mitochondria and/or ruptured mitochondria" refers to partially purified intact mitochondria and/or ruptured mitochondria produced from partially purified intact mitochondria. As used herein, the term "partially purified ruptured mitochondria" refers to ruptured mitochondria produced from partially purified intact mitochondria. According to some embodiments, partially purified intact mitochondria and/or ruptured mitochondria refer to isolated intact and/or ruptured mitochondria. As used herein, the terms "isolated intact mitochondria and/or ruptured mitochondria" and "isolated intact mitochondria and/or ruptured mitochondria derived therefrom" refers to isolated intact mitochondria and/or ruptured mitochondria produced from isolated intact mitochondria. According to some embodiments, the term "ruptured mitochondria" refers to ruptured mitochondria produced from intact partially purified or intact isolated mitochondria.

According to some embodiments, mitochondria that have undergone at least one freeze-thaw cycle refer to partially purified intact mitochondria that have undergone at least one freeze-thaw cycle and/or ruptured mitochondria produced from partially purified intact mitochondria that have undergone at least one freeze-thaw cycle.

The mitochondria according to the invention may be obtained by methods disclosed herein or by any other method known in the art. Commercially available mitochondria isolation kits include, for example Mitochondria Isolation Kit, MITOISO1 (Sigma-Aldrich), among others.

According to some embodiments, the mitochondria of the invention are functional mitochondria. According to another embodiment, partially purified mitochondria are functional mitochondria. According to another embodiment, the mitochondria of the invention are not functional. According to another embodiment, the mitochondria of the invention are isolated mitochondria. According to another embodiment, the mitochondria of the invention are intact mitochondria. According to another embodiment, the mitochondria of the invention are partially-functional. As used herein, partially-functional mitochondria refer to mitochondria lacking at least one functional property of mitochondria, such as, but not limited to, oxygen consumption. According to some embodiments, ruptured mitochondria are non-functional mitochondria. According to some embodiments, ruptured mitochondria are partially-functional mitochondria.

According to some embodiments, the term "functional mitochondria" refers to mitochondria that consume oxygen. According to another embodiment, functional mitochondria have an intact outer membrane. According to some embodiments, functional mitochondria are intact mitochondria. According to some embodiments, functional mitochondria consume oxygen at an increasing rate over time. According to some embodiments, the functionality of mitochondria is measured by oxygen consumption. According to some embodiments, oxygen consumption of mitochondria may be measured by any method known in the art such as, but not limited to, the MitoXpress fluorescence probe (Luxcel). According to some embodiments, functional mitochondria are mitochondria which display an increase in the rate of oxygen consumption in the presence of ADP and a substrate such as, but not limited to, glutamate, malate or succinate. Each possibility represents a separate embodiment of the present invention. According to some embodiments, functional mitochondria are mitochondria which produce ATP. According to some embodiments, functional mitochondria are mitochondria capable of manufacturing their own RNAs and proteins and are self-reproducing structures. According to some embodiments, functional mitochondria produce a mitochondrial ribosome and mitochondrial tRNA molecules.

As is known in the art, functional placental mitochondria participate in production of progesterone (see, for example, Tuckey R C, Placenta, 2005, 26(4):273-81). According to some embodiments, functional mitochondria are mitochondria which produce progesterone or pregnenolone. Each possibility represents a separate embodiment of the present invention. According to some embodiments, functional mitochondria are mitochondria which secrete progesterone. In a non-limiting example, mitochondria derived from placenta or placental cells grown in culture produce progesterone or pregnenolone. Each possibility represents a separate embodiment of the present invention. According to some embodiments, the mitochondria of the invention are derived from placenta or placental cells grown in culture and the mitochondria produce progesterone or pregnenolone. Each possibility represents a separate embodiment of the present invention. According to some embodiments, the production of progesterone or pregnenolone in the partially purified intact mitochondria of the invention is not impaired following a freeze-thaw cycle. According to some embodiments, the functionality of mitochondria is measured by measuring mitochondrial progesterone production or mitochondrial production of progesterone precursors such as, but not limited to, pregnenolone. Each possibility represents a separate embodiment of the present invention. Progesterone production may be measured by any assay known in the art such as, but not limited to, a radioimmunoassay (RIA).

As used herein, the term "partially purified mitochondria" refers to mitochondria separated from other cellular components, wherein the weight of the mitochondria constitutes between 20-80%, preferably 30-80%, most preferably 40-70% of the combined weight of the mitochondria and other sub-cellular fractions (as exemplified in: Hartwig et al., Proteomics, 2009, (9):3209-3214). Each possibility represents a separate embodiment of the present invention. According to another embodiment, partially purified mitochondria do not contain intact cells. According to some embodiments, the composition of the invention does not comprise intact cells.

According to another embodiment, the weight of the mitochondria in partially purified mitochondria constitutes at least 20% of the combined weight of the mitochondria and other sub-cellular fractions. According to another embodiment, the weight of the mitochondria in partially purified mitochondria constitutes between 20%-40% of the combined weight of the mitochondria and other sub-cellular fractions. According to another embodiment, the weight of the mitochondria in partially purified mitochondria constitutes between 40%-80% of the combined weight of the mitochondria and other sub-cellular fractions. According to another embodiment, the weight of the mitochondria in partially purified mitochondria constitutes between 30%-70% of the combined weight of the mitochondria and other sub-cellular fractions. According to another embodiment, the weight of the mitochondria in partially purified mitochondria constitutes between 50%-70% of the combined weight of the mitochondria and other sub-cellular fractions. According to another embodiment, the weight of the mitochondria in partially purified mitochondria constitutes between 60%-70% of the combined weight of the mitochondria and other sub-cellular fractions. According to another embodiment, the weight of the mitochondria in partially purified mitochondria constitutes less than 80% of the combined weight of the mitochondria and other sub-cellular fractions.

As used herein, the term "mitochondrial proteins" refers to proteins which originate from mitochondria, including mitochondrial proteins which are encoded by genomic DNA or mtDNA. As used herein, the term "cellular proteins" refers to all proteins which originate from the cells or tissue from which the mitochondria are produced.

As used herein, the term "isolated mitochondria" refers to mitochondria separated from other cellular components, wherein the weight of the mitochondria constitutes more than 80% of the combined weight of the mitochondria and other sub-cellular fractions. Preparation of isolated mitochondria may require changing buffer composition or additional washing steps, cleaning cycles, centrifugation cycles and sonication cycles which are not required in preparation of partially purified mitochondria. Without wishing to be bound by any theory or mechanism, such additional steps and cycles may harm the functionality of the isolated mitochondria.

According to another embodiment, the weight of the mitochondria in isolated mitochondria constitutes more than 90% of the combined weight of the mitochondria and other sub-cellular fractions. A non-limiting example of a method for obtaining isolated mitochondria is the MACS® technology (Miltenyi Biotec). Without wishing to be bound by any theory or mechanism, isolated mitochondria in which the weight of the mitochondria constitutes more than 95% of the combined weight of the mitochondria and other sub-cellular fractions are not functional mitochondria. According to another embodiment, isolated mitochondria do not contain intact cells. According to some embodiments, the mitochondria of the invention are isolated mitochondria.

As used herein, the term "intact mitochondria" refers to mitochondria comprising an outer membrane, an inner membrane, the cristae (formed by the inner membrane) and the matrix. According to some embodiments, intact mitochondria comprise mitochondrial DNA. As used herein, the term "mitoplasts" refers to mitochondria devoid of outer membrane. According to another embodiment, intactness of a mitochondrial membrane may be determined by any method known in the art. In a non-limiting example, intactness of a mitochondrial membrane is measured using the tetramethylrhodamine methyl ester (TMRM) or the tetramethylrhodamine ethyl ester (TMRE) fluorescent probes. Each possibility represents a separate embodiment of the present invention. Mitochondria that were observed under a microscope and show TMRM or TMRE staining have an intact mitochondrial outer membrane. According to some embodiments, intactness of a mitochondrial membrane is measured by assaying the presence of citrate synthase outside mitochondria. According to some embodiments, mitochondria that release citrate synthase have compromised mitochondrial intactness. According to some embodiments, intactness of a mitochondrial membrane is determined by measuring the mitochondrial rate of oxygen consumption coupled to presence of ADP. According to some embodiments, an increase in mitochondrial oxygen consumption in the presence of ADP is indicative of an intact mitochondrial membrane. According to some embodiments, intact mitochondria according to the invention are partially purified mitochondria. According to some embodiments, intact mitochondria according to the invention are isolated mitochondria. According to some embodiments, functional mitochondria are intact mitochondria.

As used herein, the term "a mitochondrial membrane" refers to a mitochondrial membrane selected from the group consisting of: the mitochondrial inner membrane, the mitochondrial outer membrane and a combination thereof.

As used herein, the term "ruptured mitochondria" refers to mitochondria in which the inner and outer mitochondrial membranes have been sheared (torn) and/or perforated and/or punctured and the like. According to some embodiments, ruptured mitochondria are mitochondria that have been sheared to more than one piece/portion. It is to be understood that ruptured mitochondria are partially purified intact mitochondria that had been ruptured by the methods described herein or any other method known in the art.

According to some embodiments, ruptured mitochondria are mitochondria in which the inner and outer mitochondrial membranes have been sheared (torn), perforated, punctured and the like and which released at least one mitochondrial constituent. According to some embodiments, rupture of partially purified intact mitochondria results in release of at least one mitochondrial constituent.

As used herein, the term "mitochondrial constituent" refers to any element comprised in mitochondria. According to some embodiments, a mitochondrial constituent is at least one element selected from the group consisting of: mitochondrial protein, mitochondrial nucleic acid, mitochondrial lipid, mitochondrial saccharide, mitochondrial structure, at least part of a mitochondrial matrix and a combination thereof. Each possibility represents a separate embodiment of the present invention.

As used herein, the term "mitochondrial structure" refers to structures and/or organelles present in mitochondria, such as, but not limited to, matrix granules, ATP-synthase particles, mitochondrial ribosomes and cristae. According to some embodiments, a mitochondrial constituent maintains at least one function of intact functional mitochondria. According to some embodiments, a mitochondrial constituent comprises a single type of mitochondrial protein, mitochondrial nucleic acid, mitochondrial lipid, mitochondrial structure or mitochondrial saccharide. Each possibility represents a separate embodiment of the present invention. According to some embodiments, a mitochondrial constituent comprises at least one functioning protein. According to some embodiments, a mitochondrial constituent comprises at least part of the mitochondrial matrix. According to some embodiments, a mitochondrial constituent comprises the entire mitochondrial matrix. According to some embodiments, a mitochondrial constituent comprises at least part of the mitochondrial matrix and at least part of the elements comprised therein, such as, but not limited to proteins, adenosine triphosphate (ATP) or ions. According to some embodiments, a mitochondrial constituent comprises at least part of the mitochondrial matrix and at least one of the following elements comprised therein: mitochondrial protein, mitochondrial nucleic acid, mitochondrial lipid, mitochondrial saccharide and a mitochondrial structure. Each possibility represents a separate embodiment of the present invention. As used herein, the term "mitochondrial matrix" refers to the viscous material within the mitochondrial inner membrane.

It is to be understood that mitochondrial constituents according to some embodiments of the present invention are elements secreted or released from mitochondria, such as, but not limited to mitochondrial proteins. According to some embodiments, mitochondrial constituents which are secreted or released from mitochondria may be retrieved by any method known in the art, such as, but not limited to, retrieving the mitochondrial constituents from a conditioned medium in which mitochondria have been incubated.

It is to be understood that ruptured mitochondria and/or mitochondrial constituents according to some embodiments of the present invention are obtained from partially purified intact mitochondria. As used herein, the terms "hypotonic", "isotonic" and "hypertonic" relate to a concentration relative to the solute concentration inside intact mitochondria.

According to other embodiments, ruptured mitochondria are obtained by exposing partially purified intact mitochondria to a hypotonic solution, such as, but not limited to, a hypotonic phosphate-buffered saline (PBS) solution. Without wishing to be bound by any theory or mechanism, exposing partially purified intact mitochondria to a hypotonic solution results in explosion or perforation of the mitochondria, thus obtaining ruptured mitochondria, possibly releasing mitochondrial constituents such as, but not limited to, at least part of the mitochondrial matrix.

According to some embodiments, ruptured mitochondria are obtained by transferring mitochondria from a hypertonic solution to a hypotonic solution. Without wishing to be bound by any theory or mechanism, transferring partially purified intact mitochondria from a hypertonic solution to a hypotonic solution results in explosion, rupture or perforation of the mitochondria, thus obtaining ruptured mitochondria, possibly releasing mitochondrial constituents such as, but not limited to, at least part of the mitochondrial matrix. In a non-limiting example, explosion, rupture or perforation of partially purified intact mitochondria may result in release of mitochondrial proteins such as citrate synthase. According to some embodiments, release of citrate synthase is used as an indication of ruptured mitochondria. According to some embodiments, mitochondrial constituents according to the present invention are released from partially purified intact mitochondria by increasing the osmotic pressure within the partially purified intact mitochondria. Without wishing to be bound by any theory or mechanism, increasing the osmotic pressure within intact mitochondria such that mitochondrial membranes are perforated and/or torn results in ruptured mitochondria and possibly in release of mitochondrial constituents according to the present invention.

According to some embodiments, a composition comprising partially purified intact mitochondria according to the present invention is formulated as a hypertonic solution. According to some embodiments, the composition of the invention comprises a hypertonic solution. According to some embodiments, a hypertonic solution according to the present invention comprises a saccharide. As used herein the term "saccharide" may refer to a saccharide, an oligosaccharide or a polysaccharide. Each possibility represents a separate embodiment of the present invention. According to some embodiments, the saccharide is sucrose. According to some embodiments, the concentration of the saccharide in the hypertonic solution according to the present invention is similar to the concentration of the saccharide in the isolation buffer. According to some embodiments, a sufficient saccharide concentration which acts to preserve mitochondrial function is sufficient for preserving mitochondria intact. According to some embodiments, the isolation buffer is hypertonic. According to other embodiments, the saccharide concentration in the hypertonic solution, according to the present invention, is a sufficient saccharide concentration for preserving mitochondria intact. According to some embodiments, the composition of the invention further comprises a sufficient saccharide concentration for preserving mitochondria intact.

According to another embodiment, a sufficient saccharide concentration for preserving mitochondria intact is a concentration of between 100 mM-400 mM, preferably between 100 mM-250 mM, most preferably between 200 mM-250 mM. Each possibility represents a separate embodiment of the present invention. According to another embodiment, a sufficient saccharide concentration for preserving mitochondria intact is between 100 mM-150 mM. According to another embodiment, a sufficient saccharide concentration for preserving mitochondria intact is between 150 mM-200 mM. According to another embodiment, a sufficient saccharide concentration for preserving mitochondria intact is between 100 mM-200 mM. According to another embodiment, a sufficient saccharide concentration for preserving mitochondria intact is between 100 mM-400 mM. According to another embodiment, a sufficient saccharide concentration for preserving mitochondria intact is between 150 mM-400 mM. According to another embodiment, a sufficient saccharide concentration for preserving mitochondria intact is between 200 mM-400 mM. According to another embodiment, a sufficient saccharide concentration for preserving mitochondria intact is at least 100 mM. Without wishing to be bound by any theory or mechanism of action, a saccharide concentration below 100 mM may not be sufficient to preserve mitochondria intact. According to some embodiments, a saccharide concentration above 100 mM is hypertonic. As used herein, a sufficient saccharide concentration for preserving mitochondria intact is a sufficient saccharide concentration for preserving mitochondrial function.

According to some embodiments, a composition comprising ruptured mitochondria according to the present invention is formulated as a hypotonic solution. According to some embodiments, the composition of the invention comprises a hypotonic solution. A non-limiting example of a hypotonic solution is Phosphate Buffered Saline (PBS). According to some embodiments, mitochondria in PBS are ruptured mitochondria. According to other embodiments, mitochondria in isolation buffer are intact mitochondria. According to some embodiments, mitochondria in an isolation buffer comprising a saccharide at a concentration sufficient for preserving mitochondria intact are intact mitochondria.

According to some embodiments, the partially purified intact mitochondria of the invention are exposed to an ion-exchanger inhibitor. According to some embodiments, the partially purified intact mitochondria of the invention are reduced in size by exposure to an ion-exchanger inhibitor. According to another embodiment, the partially purified intact mitochondria of the invention were reduced in size by exposure to an ion-exchanger inhibitor. According to some embodiments, the intact mitochondria of the invention are exposed to the ion-exchanger inhibitor following partial purification or isolation. Each possibility represents a separate embodiment of the present invention. According to some embodiments, the intact mitochondria of the invention are exposed to the ion-exchanger inhibitor during partial purification or isolation. Each possibility represents a separate embodiment of the present invention. According to other embodiments, the cells or tissue from which the intact mitochondria of the invention are derived are exposed to the ion-exchanger inhibitor prior to partial purification or isolation of the mitochondria. Each possibility represents a separate embodiment of the present invention. According to another embodiment, the ion-exchanger inhibitor is CGP37157. As used herein, the terms "CGP" and "CGP37157" are used interchangeably. Without wishing to be bound by any theory or mechanism, agents blocking the mitochondrial $Na^+/Ca^{2+}$ exchanger, such as, CGP37157 may induce mitochondrial fission, increase mitochondrial ATP production and reduce mitochondrial size. Mitochondrial fission refers to spontaneous fission or fission induced by appropriate agents such as CGP37157. According to another embodiment, the final composition of the invention is devoid of free ion-exchanger inhibitor. As used herein, a composition devoid of ion-exchanger inhibitor refers to a composition devoid of ion-exchanger inhibitor which is not bound to the mitochondria of the invention. According to some embodiments, the composition of the invention comprises an ion-exchanger inhibitor bound to the mitochondria of the invention. According to some embodiments, a composition devoid of ion-exchanger inhibitor comprises an ion-exchanger inhibitor at a concentration of less than 1 µM of, preferably less than 0.5 µM, most preferably less than 0.1 µM. Each possibility represents a separate embodiment of the present invention.

According to some embodiments, the mitochondria of the invention are derived from a different subject than the subject to whom they are administered. According to some embodiments, the mitochondria of the invention are derived from the same subject to whom they are administered. According to another embodiment, the mitochondria of the invention are from a source selected from allogeneic and xenogeneic. Each possibility represents a separate embodiment of the present invention. According to another embodiment, the mitochondria of the invention are from a source selected from syngeneic, allogeneic and xenogeneic. Each possibility represents a separate embodiment of the present invention. According to another embodiment, the mitochondria of the invention are derived from a cell or tissue from a source selected from allogeneic and xenogeneic. Each possibility represents a separate embodiment of the present invention. According to another embodiment, the mitochondria of the invention are derived from a cell or tissue from a source selected from syngeneic, allogeneic and xenogeneic. Each possibility represents a separate embodiment of the present invention.

As used herein, mitochondria of an allogeneic source refer to mitochondria derived from a different subject than the subject to be treated from the same species. As used herein, mitochondria of a xenogeneic source refer to mitochondria derived from a different subject than the subject to be treated from a different species. As used herein, the term "syngeneic" refers to genetically identical. According to some embodiments, an autologous cell is a syngeneic cell.

According to some embodiments, the mitochondria of the invention are derived from a mammalian subject. According to another embodiment, the mammalian subject is a human subject. According to another embodiment, the mitochondria of the invention are derived from a mammalian cell. According to another embodiment, the mammalian cell is a human cell. According to another embodiment, the mitochondria of the invention are derived from cells in culture. According to another embodiment, the mitochondria of the invention are derived from human cells in culture. According to another embodiment, the mitochondria of the invention are derived from a tissue.

According to some embodiments, the mitochondria of the invention are derived from a cell or a tissue selected from the group consisting of: human placenta, human placental cells grown in culture and human blood cells. Each possibility represents a separate embodiment of the present invention. According to another embodiment, the mitochondria of the invention are derived from a cell or a tissue selected from the group consisting of: placenta, placental cells grown in culture and blood cells. Each possibility represents a separate embodiment of the present invention.

According to some embodiments, ruptured mitochondria according to the present invention are derived from intact mitochondria. According to some embodiments, ruptured mitochondria according to the present invention are derived from intact partially purified mitochondria. According to some embodiments, ruptured mitochondria according to the present invention are derived from intact isolated mitochondria.

According to some embodiments, the partially purified intact mitochondria and/or ruptured mitochondria of the invention are derived from a cell or a tissue selected from the group consisting of: human placenta, human placental cells grown in culture and human blood cells. Each possibility represents a separate embodiment of the present invention. According to another embodiment, the partially purified intact mitochondria and/or ruptured mitochondria of the invention are derived from a cell or a tissue selected from the group consisting of: placenta, placental cells grown in culture and blood cells. Each possibility represents a separate embodiment of the present invention.

According to some embodiments, the mitochondrial constituent according to the present invention is produced from mitochondria derived from a cell or a tissue selected from the group consisting of: placenta, placental cells grown in culture and blood cells. Each possibility represents a separate embodiment of the present invention. According to some embodiments, the mitochondrial constituent according to the present invention is produced from mitochondria derived from a cell or a tissue selected from the group consisting of: human placenta, human placental cells grown in culture and human blood cells. Each possibility represents a separate embodiment of the present invention.

As used herein the phrases "cells grown in culture" or "a tissue grown in culture" refer to a multitude of cells or a tissue, respectively, grown in a liquid, semi-solid or solid medium, outside of the organism from which the cells or tissue derive. According to some embodiments, cells grown in culture are cells grown in bioreactors. According to a non-limiting example, cells may be grown in a bioreactor, followed by isolation of partially purified functional mitochondria from the cells.

According to another embodiment, the mitochondria of the invention have undergone a freeze-thaw cycle. According to some embodiments, the partially purified intact mitochondria of the invention have undergone a freeze-thaw cycle. According to some embodiments, ruptured mitochondria according to the invention were produced from partially purified intact mitochondria that have undergone a freeze-thaw cycle. Without wishing to be bound by any theory or mechanism, partially purified intact mitochondria that have undergone a freeze-thaw cycle demonstrate at least comparable oxygen consumption rate following thawing, as compared to control partially purified intact mitochondria that have not undergone a freeze-thaw cycle. Thus, partially purified intact mitochondria that have undergone a freeze-thaw cycle are at least as functional as control mitochondria that have not undergone a freeze-thaw cycle.

As used herein, the term "freeze-thaw cycle" refers to freezing of the mitochondria of the invention to a temperature below 0° C., maintaining the mitochondria in a temperature below 0° C. for a defined period of time and thawing the mitochondria to room temperature or body temperature or any temperature above 0° C. which enables administration according to the methods of the invention. Each possibility represents a separate embodiment of the present invention. The term "room temperature", as used herein refers to a temperature of between 18° C. and 25° C. The term "body temperature", as used herein, refers to a temperature of between 35.5° C. and 37.5° C., preferably 37° C.

According to some embodiments, the mitochondria that have undergone a freeze-thaw cycle were frozen at a temperature of at least −196° C. According to some embodiments, the mitochondria that have undergone a freeze-thaw cycle were frozen at a temperature of at least −70° C. According to some embodiments, the mitochondria that have undergone a freeze-thaw cycle were frozen at a temperature of at least −20° C. According to some embodiments, the mitochondria that have undergone a freeze-thaw cycle were frozen at a temperature of at least −4° C. According to some embodiments, the mitochondria that have undergone a freeze-thaw cycle were frozen at a temperature of at least 0° C. According to another embodiment, freezing of the mitochondria is gradual. According to some embodiment, freezing of mitochondria is through flash-freezing. As used herein, the term "flash-freezing" refers to rapidly freezing the mitochondria by subjecting them to cryogenic temperatures. In a non-limiting example, flash-freezing may include freezing using liquid nitrogen.

According to some embodiments, the mitochondria that underwent a freeze-thaw cycle were frozen for at least 30 minutes prior to thawing. According to another embodiment, the freeze-thaw cycle comprises freezing the mitochondria for at least 30, 60, 90, 120, 180, 210 minutes prior to thawing. Each possibility represents a separate embodiment of the present invention. According to some embodiments, the mitochondria that have undergone a freeze-thaw cycle were frozen for at least 1, 2, 3, 4, 5, 6, 7, 8, 9, 10, 24, 48, 72, 96, 120 hours prior to thawing. Each freezing time presents a separate embodiment of the present invention. According to some embodiments, the mitochondria that have undergone a freeze-thaw cycle were frozen for at least 4, 5, 6, 7, 30, 60, 120, 365 days prior to thawing. Each freezing time presents a separate embodiment of the present invention. According to another embodiment, the freeze-thaw cycle comprises freezing the mitochondria for at least 1, 2, 3 weeks prior to thawing. Each possibility represents a separate embodiment of the present invention. According to another embodiment, the freeze-thaw cycle comprises freezing the mitochondria for at least 1, 2, 3, 4, 5, 6 months prior to thawing. Each possibility represents a separate embodiment of the present invention.

According to some embodiments, the mitochondria that have undergone a freeze-thaw cycle were frozen at −70° C. for at least 30 minutes prior to thawing. Without wishing to be bound by any theory or mechanism, the possibility to freeze mitochondria and thaw them after a long period enables easy storage and use of the mitochondria with reproducible results even after a long period of storage. According to some embodiments, ruptured mitochondria according to the present invention are prepared/produced from partially purified intact mitochondria that have undergone a freeze-thaw cycle. According to some embodiments, ruptured mitochondria according to the present invention are prepared/produced from partially purified mitochondria.

According to another embodiment, thawing is at room temperature. According to some embodiments, thawing is at body temperature. According to another embodiment, thawing is at a temperature which enables administration according to the methods of the invention. According to another embodiment, thawing is performed gradually.

As used herein, the term "isolation buffer" refers to a buffer in which the mitochondria of the invention have been partially purified or isolated. Each possibility represents a separate embodiment of the present invention. It is to be understood that intact mitochondria according to the invention are isolated or partially purified in isolation buffer, while ruptured mitochondria are produced from isolated/partially purified intact mitochondria by methods described herein or any other method known in the art. In a non-limiting example, the isolation buffer comprises 200 mM sucrose, 10 mM Tris-MOPS and 1 mM EGTA. According to some embodiments, BSA (Bovine Serum Albumin) is added to the isolation buffer during partial purification or isolation. Each possibility represents a separate embodiment of the present invention. According to some embodiments, 0.2% BSA is added to the isolation buffer during partial purification or isolation. Each possibility represents a separate embodiment of the present invention. According to some embodiments, HSA (Human Serum Albumin) is added to the isolation buffer during partial purification or isolation. Each possibility represents a separate embodiment of the present invention. According to some embodiments, 0.2% HSA is added to the isolation buffer during partial purification or isolation. Each possibility represents a separate embodiment of the present invention. According to other embodiment, HSA or BSA is washed away from the mitochondria of the invention following partial purification or isolation. Each possibility represents a separate embodiment of the present invention. Without wishing to be bound by any mechanism or theory, freezing mitochondria within the isolation buffer saves time and isolation steps, as there is no need to replace the isolation buffer with a freezing buffer prior to freezing or to replace the freezing buffer upon thawing.

According to another embodiment, the mitochondria that underwent a freeze-thaw cycle were frozen within a freezing buffer. According to another embodiment, the partially purified intact mitochondria that underwent a freeze-thaw cycle were frozen within the isolation buffer. According to another embodiment, the partially purified intact mitochondria that underwent a freeze-thaw cycle were frozen within a buffer comprising the same constituents as the isolation buffer.

According to another embodiment, the freezing buffer comprises a cryoprotectant. According to some embodiments, the cryoprotectant is a saccharide, an oligosaccharide or a polysaccharide. Each possibility represents a separate embodiment of the present invention. According to another embodiment, the saccharide concentration in the freezing buffer is a sufficient saccharide concentration which acts to preserve mitochondrial function. According to another embodiment, the isolation buffer comprises a saccharide. According to another embodiment, the saccharide concentration in the isolation buffer is a sufficient saccharide concentration which acts to preserve mitochondrial function. According to another embodiment, the saccharide concentration in the isolation buffer is a sufficient saccharide concentration which acts to keep mitochondria intact. According to another embodiment, the saccharide concentration in the freezing buffer is a sufficient saccharide concentration which acts to keep mitochondria intact. According to another embodiment, the saccharide is sucrose. Without wishing to be bound by any theory or mechanism, partially purified intact mitochondria that have been frozen within a freezing buffer or isolation buffer comprising sucrose demonstrate at least comparable oxygen consumption rate following thawing, as compared to control mitochondria that have not undergone a freeze-thaw cycle or that have been frozen within a freezing buffer or isolation buffer without sucrose.

According to some embodiments, ruptured mitochondria underwent a freeze-thaw cycle. According to some embodiments, the ruptured mitochondria that underwent a freeze-thaw cycle were frozen within a freezing buffer. According to some embodiments, the ruptured mitochondria that underwent a freeze-thaw cycle were frozen within a hypotonic solution, such as, but not limited to PBS.

According to some embodiments, the ruptured mitochondria that underwent a freeze-thaw cycle were frozen within the isolation buffer. According to another embodiment, the ruptured mitochondria that underwent a freeze-thaw cycle were frozen within a buffer comprising the same constituents as the isolation buffer. According to some embodiments, the mitochondrial constituent that underwent a freeze-thaw cycle was frozen within the isolation buffer.

According to some embodiments, the composition further comprises a carrier. According to some embodiments, the composition further comprises a bioactive agent selected from the group consisting of: stem cell, growth factor, ion exchange inhibitor, immunosuppressive drug, an antioxidant and a combination thereof. Each possibility of bioactive agent represents a separate embodiment of the invention.

According to some embodiments, the stem cell is selected from the group consisting of: neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts, neurons, oligodendrocytes, astrocytes, Schwann cells, skeletal muscle cells, cardiomyocytes, hepatocytes and a combination thereof. Each type of stem cell represents a separate embodiment of the present invention.

In other embodiments, the ion exchange inhibitor is CGP37157. According to some embodiments, CGP37157 induces mitochondrial fission. According to some embodiments the growth factor is Vascular Endothelial Growth Factor (VEGF), basic Fibroblast Growth Factor (bFGF) and a combination thereof. According to some embodiments, the immunosuppressive agent is selected from the group consisting of: a glucocorticoid drug, a cytostatic agent, an alkylating agent, an anti-metabolite, methotrexate, azathioprine, mercaptopurine, a cytotoxic antibody, cyclosporin, tacrolimus, sirolimus, interferons, mycophenolate and a combination thereof. Each possibility of immnosuppressive agent represents a separate embodiment of the present invention.

According to some embodiments, the antioxidant is selected from the group consisting of: Vitamin A, Vitamin C, Vitamin E, Coenzyme Q10, N-acetylcysteine, Curcumin, Selenium, and a combination thereof. Each antioxidant represents a separate embodiment of the present invention.

According to some embodiments, the term "inducing angiogenesis" or "induction of angiogenesis," means that angiogenesis is initiated or enhanced. Each possibility represents a separate embodiment of the present invention. According to some embodiments, inducing is in an ischemic and/or a nonischemic tissue. Each possibility represents a separate embodiment of the present invention. Therefore, in some embodiments, when a nonischemic or ischemic tissue is not already undergoing angiogenesis, the present method provides for initiation of angiogenesis in the nonischemic tissue. Each possibility represents a separate embodiment of the present invention. However, in other embodiments, when a nonischemic or ischemic tissue is already undergoing angiogenesis, the present method provides a means by which the level of angiogenesis is enhanced or heightened. Each possibility represents a separate embodiment of the present invention.

Angiogenesis according to some embodiments refers to de-novo blood-vessel formation or to formation of new blood vessels by the splitting of existing ones. Each possibility represents a separate embodiment of the present invention. According to some embodiments, angiogenesis according to the invention includes collateral blood vessels formation.

According to some embodiments, inducing angiogenesis is enhancing the level of blood perfusion. According to some embodiments, inducing angiogenesis is restoring blood flow. According to some embodiments, inducing angiogenesis is inducing blood flow. According to some embodiments, inducing angiogenesis is inducing growth of new blood vessels from pre-existing vessels. According to some embodiments, inducing angiogenesis is inducing neovascularization. According to some embodiments, inducing angiogenesis is enhancing neovascularization. According to some embodiments, inducing angiogenesis is enhancing growth of new blood vessels from pre-existing vessels. According to some embodiments, inducing angiogenesis refers to at least one activity selected from the group consisting of: enhancing the level of blood perfusion, restoring blood flow, inducing blood flow, inducing growth of new blood vessels from pre-existing vessels, enhancing growth of new blood vessels from pre-existing vessels, inducing neovascularization, enhancing neovascularization and a combination thereof. Each possibility represents a separate embodiment of the present invention.

According to some embodiments, inducing angiogenesis is inducing angiogenesis at an ischemic tissue. According to some embodiments, inducing angiogenesis is inducing angiogenesis at a tissue at risk of being affected with an ischemia. According to some embodiments, inducing angiogenesis is inducing angiogenesis at a tissue at risk of being affected with an ischemic damage. According to some embodiments, inducing angiogenesis is inducing angiogenesis at a tissue at risk of being affected by a vascular occlusion. According to some embodiments, inducing angiogenesis is inducing angiogenesis in the proximity of a tissue affected by ischemia or vascular occlusion. According to some embodiments, inducing angiogenesis is inducing angiogenesis at a tissue with an impaired vascularization. According to some embodiments, inducing angiogenesis is inducing angiogenesis at a tissue afflicted with a pathology which would benefit from angiogenesis.

According to some embodiments, a tissue at risk of being affected with an ischemic damage and/or at risk of being affected by a vascular occlusion is cardiac tissue having impaired cardio-vascularization. Each possibility represents a separate embodiment of the present invention. According to some embodiments, a tissue at risk of being affected with an ischemic damage and/or at risk of being affected by a vascular occlusion is cardiac tissue at risk of having a myocardial infarction and/or ischemic heart disease. Each possibility represents a separate embodiment of the present invention.

As used herein, impaired cardio-vascularization refers to reduced blood flow in coronary veins and/or arteries, and/or to reduced blood supply to cardiac tissue, relatively to a healthy subject, due to innate and/or acquired pathologies, such as, but not limited to coronary heart disease (CHD). According to some embodiments, cardiac tissue having impaired cardio-vascularization is a cardiac tissue having increased risk of myocardial infarction and/or ischemic heart disease. Each possibility represents a separate embodiment of the present invention. Without wishing to be bound by any theory or mechanism, the methods of the invention may be used to induce angiogenesis in a subject afflicted with impaired cardio-vascularization, thus preventing or reducing the chance and/or reducing the severity of ischemic damage and/or vascular occlusion resulting from impaired cardio-vascularization. According to some embodiments, the methods of the invention may be used to prevent or reduce probability of and/or reduce severity of myocardial infarction, ischemic heart disease or any other heart condition resulting from impaired cardio-vascularization. Each possibility represents a separate embodiment of the present invention. According to some embodiments, the present invention provides a method of treating impaired cardio-vascularization, the method comprising administering to a subject afflicted with impaired cardio-vascularization a therapeutically effective amount of a composition comprising partially purified intact mitochondria and/or ruptured mitochondria derived therefrom; wherein said partially purified intact mitochondria have undergone at least one freeze-thaw cycle. Each possibility represents a separate embodiment of the present invention.

According to some embodiments, a subject having impaired cardio-vascularization is a subject in need of coronary bypass surgery. According to some embodiments, the methods of the invention may be used to replace or augment coronary bypass surgery. Each possibility represents a separate embodiment of the present invention.

According to some embodiments, administering the mitochondrial composition of the invention to the heart of a subject obviates and/or delays the need for coronary bypass surgery in a subject in need thereof. Each possibility represents a separate embodiment of the present invention. According to some embodiments, using the methods of the invention to treat a subject having impaired cardio-vascularization obviates and/or delays the need for coronary bypass surgery in a subject in need thereof. Each possibility represents a separate embodiment of the present invention. Without wishing to be bound by any theory or mechanism, administering the mitochondrial composition of the invention to the heart of a subject having impaired cardio-vascularization may induce angiogenesis of coronary blood-vessels, thus increasing blood flow in the heart and obviating or delaying the need of coronary bypass surgery as treatment of impaired cardio-vascularization. According to some embodiments, treating according to the present invention is inducing formation of a blood vessel bypass. According to some embodiments, inducing formation of a blood vessel bypass is inducing formation of a coronary artery bypass. According to some embodiments, formation of a coronary artery bypass using the methods of the invention obviates or delays the need for a coronary bypass surgery. Each possibility represents a separate embodiment of the present invention.

According to some embodiments, the tissue is a tissue afflicted with a pathology which would benefit from angiogenesis. According to some embodiments, the tissue is an ischemic tissue. According to some embodiments, the tissue is a tissue at risk of becoming ischemic. According to some embodiments, the tissue is a tissue at risk of being affected by a vascular occlusion. According to some embodiments, the tissue is in proximity to an ischemic site. According to some embodiments, the tissue is in proximity to a site susceptible to ischemia. According to some embodiments, the tissue is an in-vivo tissue. According to some embodiments, the tissue is an ex-vivo tissue. According to some embodiments, the ex-vivo tissue is selected from the group consisting of: a tissue graft, a tissue grown in culture, an engineered tissue and a combination thereof.

According to some embodiments, the tissue is a connective tissue. According to some embodiments, the tissue is a muscle tissue. According to some embodiments, the tissue is a cardiac tissue. According to some embodiments, the tissue is an adipose tissue. According to some embodiments, the tissue is a subcutaneous tissue. According to some embodiments, the tissue is a skeletal muscle. According to some embodiments, the tissue is a muscle. According to some embodiments, the tissue is the cardiac muscle. According to some embodiments, the tissue is skin. According to some embodiments, the tissue is a scalp. According to some embodiments, the tissue is a brain.

According to some embodiments, the tissue is selected from the group consisting of: connective tissue, adipose tissue, subcutaneous tissue, skin tissue, cardiac muscle, skeletal muscle, scalp, brain tissue and a combination thereof. Each possibility represents a separate embodiment of the present invention.

According to some embodiments, a tissue afflicted with a pathology which would benefit from angiogenesis is an ischemic tissue. According to some embodiments, a tissue afflicted with a pathology which would benefit from angiogenesis is a tissue at risk of becoming ischemic. According to some embodiments, a tissue afflicted with a pathology which would benefit from angiogenesis is a tissue at risk of being affected by a vascular occlusion.

According to some embodiments, arteries at an ischemic tissue display at least one of: arterial narrowing, arterial hardening, arterial occlusion and a combination thereof. Each possibility represents a separate embodiment of the present invention.

According to some embodiments, the enhanced level of perfusion of blood to the nonischemic tissue is maintained upon induction of ischemia to the tissue. According to some embodiments, the presence of tissue ischemia at the time of administration of the mitochondrial composition is considered an essential precondition to inducing angiogenesis.

The term "ischemia", as used herein, refers to a restriction in blood supply to tissues or organs, causing a shortage of oxygen and glucose required for cellular metabolism. Ischemia may result in damage or death of cells, leading to tissue or organ dysfunction. Ischemia may result from a number of causes, such as, but not limited to: vascular narrowing, vascular hardening, vascular injury, vascular occlusion (caused by, e.g., atherosclerosis, plaque formation or thrombosis), tachycardia, hypotension hypoglycemia, anemia and sickle cell disease.

According to some embodiments, the method of the invention is applied in subjects suffering from vascular atherosclerotic disease, trauma, surgical procedures, and/or other indications that cause vascular occlusion in non-ischemic tissue.

According to some embodiments, an ischemic tissue is a tissue comprising narrowed arteries. According to some embodiments, an ischemic tissue is a tissue comprising hardened arteries. According to some embodiments, an ischemic tissue is a tissue comprising occluded arteries. According to some embodiments, an ischemic tissue is a tissue comprising injured arteries. According to some embodiments, an ischemic tissue is a tissue which is not receiving sufficient blood supply to support metabolic demand. According to some embodiments, an ischemic tissue is a tissue comprising decreased vascularization as compared to normal vascularization. According to some embodiments, an ischemic tissue is a tissue comprising at least one of: narrowed arteries, hardened arteries, occluded arteries, injured arteries and a combination thereof. According to some embodiments, the terms "ischemic tissue" and "ischemic site", as used herein, are used interchangeably. According to some embodiments, an ischemic tissue is a tissue suffering from ischemia.

According to some embodiments, a subject in need thereof is a subject afflicted with ischemia. According to some embodiments, a subject in need thereof is a subject at risk of being afflicted with ischemia. According to some embodiments, a subject in need thereof is suffering from a pathology which would benefit from angiogenesis. According to some embodiments, a subject in need thereof is afflicted with a condition selected from the group consisting of: critical limb ischemia, peripheral artery disease, Buerger's disease, myocardial infarction, traumatic brain injury, cerebrovascular accident and a combination thereof. Each possibility represents a separate embodiment of the invention. According to some embodiments, a subject in need thereof is suffering from a non-life-threatening condition such as hair loss. According to another embodiment, the pathology which would benefit from angiogenesis is hair loss.

According to some embodiments, a subject afflicted with critical limb ischemia (CLI) is suffering from pain at the site of ischemia. According to some embodiments, a subject afflicted with CLI is suffering from numbness in the feet. According to some embodiments, a subject afflicted with CLI is suffering from shiny, smooth, dry skin of the legs or feet. According to some embodiments, a subject afflicted with CLI is suffering from thickening of the toenails. According to some embodiments, a subject afflicted with CLI is suffering from absent or diminished pulse in the legs or feet. According to some embodiments, a subject afflicted with CLI is suffering from open sores. According to some embodiments, a subject afflicted with CLI is suffering from a chronic limb skin infection. According to some embodiments, a subject afflicted with CLI is suffering from chronic ulcers. According to some embodiments, a subject afflicted with CLI is suffering from dry gangrene (dry, black skin) of the legs or feet. According to some embodiments, a subject afflicted with CLI is suffering from tissue loss at the site of ischemia. According to some embodiments, a subject afflicted with CLI is suffering from ischemic neuropathy.

According to some embodiments, peripheral vascular disease (PVD) is synonymous with peripheral arterial disease (PAD), and peripheral artery occlusive disease (PAOD). According to some embodiments, a subject afflicted with PAD suffers from symptoms such as but not limited to: pain, achiness, fatigue, burning, or discomfort in the feet muscles, calves muscles, or thighs muscles. According to some embodiments, these symptoms appear during walking or exercise and go away after several minutes of rest. According to some embodiments, a subject afflicted with PAD suffers from impotence. According to some embodiments, a subject afflicted with PAD suffers from decreased blood pressure in an affected limb. According to some embodiments, a subject afflicted with PAD suffers from hair loss on the legs or feet.

According to some embodiments, a subject afflicted with Buerger's disease suffers from recurrent acute and chronic inflammation of arteries and veins of the hands and feet. According to some embodiments, a subject afflicted with Buerger's disease suffers from recurrent acute and chronic thrombosis of arteries and veins of the hands and feet. According to some embodiments, Buerger's disease mainly affects small and medium arteries.

According to some embodiments, a subject afflicted with myocardial infarction (MI) suffers from occlusion of a coronary artery. According to some embodiments, a subject afflicted with MI suffers from ischemia of the heart muscle. According to some embodiments, a subject afflicted with MI suffers from symptoms such as, but not limited to: chest pain, shortness of breath, nausea, vomiting, palpitations, sweating, and anxiety, weakness, a feeling of indigestion, and fatigue.

According to some embodiments, a subject afflicted with traumatic brain injury suffers from alterations in cerebral blood flow. According to some embodiments, a subject afflicted with traumatic brain injury suffers from alterations in the intra-skull pressure. According to some embodiments, a subject afflicted with traumatic brain injury suffers from edema. According to some embodiments, a subject afflicted with traumatic brain injury suffers from axonal injury According to some embodiments, a subject afflicted with traumatic brain injury suffers from hematoma and/or hemorrhage.

According to some embodiments, a subject afflicted with stroke cerebrovascular accident (CVA) suffers from loss of brain function. According to some embodiments, the symptoms of CVA are due to a disturbance in blood supply to the brain. According to some embodiments, CVA is caused by ischemia. According to some embodiments, CVA is caused by hemorrhage.

According to some embodiments, a subject afflicted with hair-loss suffers from decreased blood supply to the scalp.

According to some embodiments, a pathology which would benefit from angiogenesis refers to a pathology which is characterized by and/or results from insufficient blood supply. Each possibility represents a separate embodiment of the present invention. According to some embodiments, angiogenesis-dependent pathology refers to a pathology which is characterized by and/or results from ischemia. Each possibility represents a separate embodiment of the present invention.

According to some embodiments, examples of pathologies which would benefit from angiogenesis include but are not limited to: delayed wound-healing, delayed ulcer healing, reproduction associated disorders, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical limb ischemia, critical leg ischemia, lower extremity ischemia, cerebral ischemia, cerebrovascular disease, traumatic brain injury, cerebrovascular accident (CVA), hair-loss, retinopathy, retinal repair, remodeling disorder, Von Hippel-Lindau syndrome, diabetes, hereditary hemorrhagic telengiectasia, ischemic vascular disease, Buerger's disease, and ischemia associated with neurodegenerative disease such as Parkinson's and Alzheimer's disease, mitochondria-dysfunction associated disorders and mutations in mitochondrial DNA or genomic DNA encoding mitochondrial elements. Each possibility represents a separate embodiment of the invention.

According to some embodiments, induction of angiogenesis at a target site (or target tissue) treats a pathology (e.g., disease) characterized by insufficient angiogenesis (as described hereinabove) in a subject's ischemic tissue.

According to some embodiments, the composition of the invention is delivered to a normoperfused tissue prior to the occurrence of ischemia and thus stimulates the neovascularization process and preserves blood perfusion once ischemia develops. According to some embodiments, the composition of the invention is delivered to a normoperfused tissue and induces neovascularization in nonischemic tissue. According to some embodiments, the composition of the invention induces angiogenesis in non-ischemic tissue and in ischemic tissue.

Methods for determining whether a nonischemic tissue is at risk of suffering ischemic damage are well known to those skilled in the art, and include but are not limited to: clinical evaluation (history and physical examination), Doppler, treadmill test to evaluate time to development of symptoms (e.g., pain), CT scan, NMR angiography, 31P NMR spectroscopy, and contrast angiograms.

According to some embodiments, administering is contacting an ischemic tissue with the composition of the invention. According to some embodiments, administering is contacting a tissue at risk of being affected with an ischemic damage with the composition of the invention. According to some embodiments, administering is contacting a tissue at risk of being affected by a vascular occlusion with the composition of the invention. According to some embodiments, administering is contacting blood vessels in the proximity of a tissue affected by ischemia or vascular occlusion with the composition of the invention. According to some embodiments, administering is contacting blood vessels in the proximity of a tissue at risk of being affected with an ischemic damage with the composition of the invention.

According to some embodiments, administering is injecting the composition of the invention into a tissue afflicted with a pathology which would benefit from angiogenesis. According to some embodiments, administering is topically contacting the site of a pathology which would benefit from angiogenesis with the composition of the invention. According to some embodiments, administering is injecting the composition of the invention into an artery which supplies blood to a tissue afflicted with a pathology which would benefit from angiogenesis. According to some embodiments, administering is injecting the composition of the invention into a vein through which blood is drained from a tissue afflicted with a pathology which would benefit from angiogenesis. According to some embodiments, administering is systemically injecting the composition of the invention to a subject afflicted with a pathology which would benefit from angiogenesis.

Any suitable route of administration may be used for the composition of the present invention, including but not limited to topical and systemic routes. According to some embodiments, administering is administering systematically. According to some embodiments, the composition is formulated for systemic administration.

According to another embodiment, administration systemically is through a parenteral route. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to some embodiments, parenteral administration is administration intravenously, intra-arterially, administering into a blood-vessel wall, intramuscularly, intraperitoneally, intradermally, intravitreally, transdermally or subcutaneously. Each of the abovementioned administration routes represents a separate embodiment of the present invention. According to another embodiment, parenteral administration is performed by bolus injection. According to another embodiment, parenteral administration is performed by continuous infusion.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

According to another embodiment, systemic administration of the composition is through injection. For administration through injection, the composition may be formulated in an aqueous solution, for example in a physiologically compatible buffer including but not limited to Hank's solution, Ringer's solution, or physiological salt buffer. Formulations for injection may be presented in unit dosage forms, for example, in ampoules, or in multi-dose containers with, optionally, an added preservative. According to another embodiment, administration is through convection enhanced delivery (CED).

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate, triglycerides, or liposomes.

In alternative embodiments the composition of the invention is introduced by injection. According to some embodiments, composition of the invention is injected systemically and reaches the target tissue via the circulatory system. According to some embodiments, the composition of the invention is injected into an ischemic site. According to some embodiments, the composition of the invention is injected into a blood vessel. According to some embodiments, the composition of the invention is injected into an artery. According to some embodiments, the composition of the invention is injected into the lymphatic system. According to some embodiments, the blood vessel is in proximity to a pathology which would benefit from angiogenesis affected tissue or a tissue affected by artery narrowing, artery hardening, or both. According to some embodiments, the blood vessel is a narrowed artery, hardened artery, or both.

According to some embodiments, the composition delivered in a controlled release system is formulated for intravenous infusion, implantable osmotic pump, transdermal patch, liposomes, or other modes of administration. In one embodiment, a pump is used. In yet another embodiment, a controlled release system can be placed in proximity to the therapeutic target, thus requiring only a fraction of the systemic dose.

According to another embodiment, the composition is administered intravenously, and is thus formulated in a form suitable for intravenous administration. According to another embodiment, the composition is administered intra-arterially, and is thus formulated in a form suitable for intra-arterial administration. As a non-limiting example, intra-arterial administration may be injection into a heart artery during catheterization. According to another embodiment, the composition is administered intramuscularly, and is thus formulated in a form suitable for intramuscular administration. As a non-limiting example, intramuscular administration may be injecting into a muscle at several locations in the same limb.

According to another embodiment, the composition is administered into a blood vessel wall. According to some embodiments, the composition is formulated in a form suitable for administration into a blood vessel wall. According to some embodiments, the composition of the invention is administered via injection into a blood vessel wall. Without wishing to be bound by any mechanism or theory, administering into a blood-vessel wall enables topical administration to the treated blood vessel.

According to another embodiment, parenteral administration is through inhalation. For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. The preferred mode of administration will depend upon the particular indication being treated and will be apparent to one of skill in the art. According to some embodiments, the composition of the invention is formulated for inhalation.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the compound and a suitable powder base, such as lactose or starch.

Solid dosage forms for oral administration include capsules, tablets, pill, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration. The term "topical administration", as used herein, refers to administration through body surfaces. Non-limiting examples of formulations for topical use include cream, ointment, lotion, gel, foam, suspension, aqueous or cosolvent solutions, salve, liposome and sprayable liquid form. Other suitable topical product forms for the compositions of the present invention include, for example, emulsion, mousse, lotion, solution and serum. The composition may also form part of a patch for transdermal application.

According to some embodiments, the composition of the invention is administered in dose ranges from about 0.1 mg/kg to about 1 g/kg of body weight. According to some embodiments, the dosage is in a range of 50-500 mg/day. According to some embodiments, the dosage is in a range of 50-150 mg/day. According to some embodiments, the dosage is in a range of 100-200 mg/day. According to some embodiments, the dosage is in a range of 150-250 mg/day. According to some embodiments, the dosage is in a range of 200-300 mg/day. According to some embodiments, the dosage is in a range of 250-400 mg/day. According to some embodiments, the dosage is in a range of 300-500 mg/day. According to some embodiments, the dosage is in a range of 350-500 mg/day. As used herein, the term "the dosage" refers to the dosage of the composition of the invention.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. According to some embodiments, the dosage is 0.1 mg/day. According to some embodiments, the dosage is 1 mg/day. According to some embodiments, the dosage is 0.530 mg/day. According to some embodiments, the dosage is 0.05 mg/day. According to some embodiments, the dosage is 50 mg/day. According to some embodiments, the dosage is 10 mg/day. According to some embodiments, the dosage is 20-70 mg/day. According to some embodiments, the dosage is 5 mg/day.

According to some embodiments, the dosage is 1-90 mg/day. According to some embodiments, the dosage is 1-90 mg/2 days. According to some embodiments, the dosage is 1-90 mg/3 days. According to some embodiments, the dosage is 1-90 mg/4 days. According to some embodiments, the dosage is 1-90 mg/5 days. According to some embodiments, the dosage is 1-90 mg/6 days. According to some embodiments, the dosage is 1-90 mg/week. According to some embodiments, the dosage is 1-90 mg/9 days. According to some embodiments, the dosage is 1-90 mg/11 days. According to some embodiments, the dosage is 1-90 mg/14 days.

In one embodiment, depending on the severity and responsiveness of the condition to be treated, dosing can be of a single or a plurality of administrations, with course of treatment lasting from several days to several weeks or until cure is effected or diminution of the disease state is achieved. In one embodiment, the amount of a composition to be administered will, of course, be dependent on the subject being treated, the severity of the affliction, the manner of administration, the judgment of the prescribing physician, etc.

According to some embodiments, administration is repeated after 24 hours, 48 hours, 72 hours, 7 days, 14 days, 30 days, 60 days, 90 days, 180 days or 1 year. Each possibility represents a separate embodiment of the present invention.

In one embodiment, compositions of the present invention are presented in a pack or dispenser device, such as an FDA approved kit, which contains one or more unit dosage forms containing the composition of the invention. In one embodiment, the pack, for example, comprises a metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

According to another aspect, the present invention provides a method for treating a subject afflicted with a pathology which would benefit from angiogenesis, wherein the method comprises: providing a composition comprising partially purified intact mitochondria and/or ruptured mitochondria derived therefrom, wherein said partially purified intact mitochondria have undergone at least one freeze-thaw cycle; and administering the composition to a tissue afflicted with a pathology which would benefit from angiogenesis. Each possibility represents a separate embodiment of the present invention.

According to another embodiment, the present invention provides a method for treating a subject afflicted with a pathology which would benefit from angiogenesis, wherein the method comprises: providing a composition comprising ruptured mitochondria; and administering the composition to a tissue afflicted with a pathology which would benefit from angiogenesis. According to another embodiment, the present invention provides a method for treating a subject afflicted with a pathology which would benefit from angiogenesis, wherein the method comprises: providing a composition comprising partially purified intact mitochondria, wherein said partially purified intact mitochondria have undergone at least one freeze-thaw cycle; and administering the composition to a tissue afflicted with a pathology which would benefit from angiogenesis.

According to another embodiment, the present invention provides a method for treating a subject afflicted with a pathology which would benefit from angiogenesis, wherein the method comprises: providing a composition comprising mitochondria and administering the composition to a tissue afflicted with a pathology which would benefit from angiogenesis.

According to some embodiments, a subject to be treated according to the present invention is a mammal. According to some embodiments, a subject to be treated according to the present invention is a human subject. According to some embodiments, mitochondria are obtained from cells derived from a healthy tissue of the subject. Each possibility represents a separate embodiment of the present invention.

According to some embodiments, a tissue afflicted with a pathology which would benefit from angiogenesis is an ischemic tissue. According to some embodiments, treating is inducing angiogenesis near or at an ischemic site. According to some embodiments, treating is enhancing angiogenesis near or at an ischemic site. According to some embodiments, treating is inhibiting the spread of ischemia. According to some embodiments, treating is arresting or decreasing cell death at an ischemic site.

According to some embodiments, the term "treating" refers to causing the reduction, remission, or regression of a pathology which would benefit from angiogenesis. Each possibility represents a separate embodiment of the present invention. According to some embodiments, those of skill in the art will understand that various methodologies and assays can be used to assess the development of a pathology which would benefit from angiogenesis, and similarly, various methodologies and assays may be used to assess the reduction, remission or regression of the pathology.

According to some embodiments, treating is enhancing or restoring blood flow to a site of artery narrowing, artery hardening, artery occlusion or a combination thereof. Each possibility represents a separate embodiment of the present invention. According to some embodiments, treating is enhancing or restoring blood flow in an ischemic tissue. Each possibility represents a separate embodiment of the present invention. According to some embodiments, treating is enhancing or restoring blood flow to a tissue afflicted with a pathology which would benefit from angiogenesis. Each possibility represents a separate embodiment of the present invention. According to some embodiments, treating is enhancing or restoring blood flow to a muscle affected by ischemia or in proximity to a site of artery narrowing, artery hardening, artery occlusion or a combination thereof. Each possibility represents a separate embodiment of the present invention. According to some embodiments, treating is enhancing or restoring muscle function in a muscle affected by ischemia or in proximity to a site of artery narrowing, artery hardening, artery occlusion or a combination thereof. Each possibility represents a separate embodiment of the present invention. According to some embodiments, treating is enhancing or restoring muscle mass in a muscle affected by ischemia or in proximity to a site of artery narrowing, artery hardening, artery occlusion or a combination thereof. Each possibility represents a separate embodiment of the present invention. According to some embodiments, muscle is skeletal muscle. According to some embodiments, muscle is cardiac muscle.

According to some embodiments, treating is enhancing or restoring blood flow to a brain affected by ischemia or in proximity to a site of artery narrowing, artery hardening, artery occlusion or a combination thereof. According to some embodiments, treating is slowing advancement of brain damage. According to some embodiments, treating is enhancing or restoring brain function in a muscle affected by ischemia or in proximity to a site of artery narrowing, artery hardening, artery occlusion or a combination thereof. Each possibility represents a separate embodiment of the present invention.

According to some embodiments, treating is inducing or restoring connective tissue integrity in a connective tissue affected by ischemia or in proximity to a site of artery narrowing, artery hardening, artery occlusion or a combination thereof. Each possibility represents a separate embodiment of the present invention. According to some embodiments, treating is inducing or restoring skin in an epithelial tissue affected by ischemia or in proximity to a site of artery narrowing, artery hardening, artery occlusion or a combination thereof. According to some embodiments, treating is reducing inflammation in a tissue affected by ischemia or in proximity to a site of artery narrowing, artery hardening, artery occlusion or a combination thereof.

According to some embodiments, treating is reducing the risk of amputation. According to some embodiments, treating is reducing pain caused by a pathology which would benefit from angiogenesis. According to some embodiments, treating is improving or restoring gait in a subject suffering from a pathology which would benefit from angiogenesis. According to some embodiments, treating is reducing risk of an increase in size of a pathology which would benefit from angiogenesis. According to some embodiments, treating is reducing hair loss. According to some embodiments, treating is inducing hair growth. According to some embodiments, treating is inducing angiogenesis in the proximity of hair follicles.

According to some embodiments, treating is selected from the group consisting of: inducing angiogenesis, enhancing angiogenesis, enhancing blood flow, restoring blood flow, inducing formation of a blood vessel bypass, increasing endogenous mitochondrial activity in a tissue afflicted with a pathology which would benefit from angiogenesis, reducing risk of critical limb ischemia, enhancing muscle function, restoring muscle function, inducing connective tissue integrity, restoring connective tissue integrity, restoring skin, reducing inflammation, reducing the risk of amputation, reducing pain caused by a pathology which would benefit from angiogenesis, reducing risk of blood starvation, reducing risk of developing major infections, inducing activity of endogenous mitochondria, enhancing activity of endogenous mitochondria, slowing advancement of brain damage, reducing risk of an increase in size of said pathology which would benefit from angiogenesis, reducing risk of an increase in size of a pathology which would benefit from angiogenesis and any combination thereof. Each possibility represents a separate embodiment of the present invention. According to some embodiments, treating is treating a tissue afflicted with a pathology which would benefit from angiogenesis. As used herein, activity of endogenous mitochondria refers to at least one function performed by functional endogenous mitochondria of the treated subject, such as, but not limited to, citrate synthase activity, COXI activity, oxygen consumption and the like.

According to some embodiments, a tissue afflicted with a pathology which would benefit from angiogenesis is a tissue at risk of being affected with an ischemic damage or of being affected by a vascular occlusion. According to some embodiments, the term "treating" refers to inhibiting, preventing or arresting the development of a pathology which would benefit from angiogenesis. Each possibility represents a separate embodiment of the present invention.

According to some embodiments, a subject having a pathology which would benefit from angiogenesis, yet not fully advanced, comprises tissues or sites at risk of being affected with an ischemic damage or of being affected by a vascular occlusion. Each possibility represents a separate embodiment of the present invention. According to some embodiments, those of skill in the art are aware of methods of assessing the advancement of a pathology which would benefit from angiogenesis. According to some embodiments, those of skill in the art are aware of methods of assessing the risk of a tissue or site being affected with an ischemic damage or of being affected by a vascular occlusion.

According to some embodiments, treating is reducing risk of a heart attack. According to some embodiments, treating is reducing risk of cardiac infarction. According to some embodiments, treating is arresting development of a cardiac infarction. According to some embodiments, treating is reducing risk of damage associated with ischemia. According to some embodiments, treating is preventing skin lesions at a site at risk of being affected with an ischemic damage or of being affected by a vascular occlusion. According to some embodiments, treating is preventing inflammation at the site at risk of being affected with an ischemic damage or of being affected by a vascular occlusion. According to some embodiments, treating is reducing risk of cell death at a site at risk of being affected with an ischemic damage or of being affected by a vascular occlusion.

According to some embodiments, the present invention provides a method for reducing the risk of critical limb ischemia (CLI) in a subject afflicted with peripheral artery disease (PAD), comprising: providing a composition comprising partially purified intact mitochondria and/or ruptured mitochondria derived therefrom, wherein said partially purified intact mitochondria have undergone at least one freeze-thaw cycle; and administering the composition to a tissue afflicted with peripheral artery disease, thereby reducing the risk of critical limb ischemia in a subject afflicted with peripheral artery disease.

According to some embodiments, treating is reducing the risk of CLI in a subject afflicted with PAD. According to some embodiments, CLI is viewed as an advance stage of PAD. According to some embodiments, treating with the composition of the invention is inhibiting the process of narrowing, hardening or occluding arteries in an affected limb. According to some embodiments, treating is reducing the risk of tissue (such as muscle) blood starvation. According to some embodiments, treating is reducing the risk of developing major infections and open wounds.

Without wishing to be bound by any theory or mechanism, treating a subject afflicted with a pathology which would benefit from angiogenesis using the composition of the invention results in formation of new blood vessels. New blood vessels may form at the site of ischemia or a site at the risk of being affected with an ischemic damage or of being affected by a vascular occlusion. Formation of new blood vessels restores blood flow or blood perfusion to the ischemic tissue or the tissue at the risk of being affected with an ischemic damage or of being affected by a vascular occlusion. Restoration of blood flow treats ischemia or reduces risk of ischemia at a site with a risk of being affected with an ischemic damage or of being affected by a vascular occlusion.

According to yet another aspect, the present invention provides a method for enhancing engraftment of a tissue graft, wherein the method comprises: providing a composition comprising partially purified intact mitochondria and/or ruptured mitochondria derived therefrom, wherein said partially purified intact mitochondria have undergone at least one freeze-thaw cycle; and administering the composition to a subject engrafted with the tissue graft. Each possibility represents a separate embodiment of the present invention.

According to yet another embodiment, the present invention provides a method for enhancing engraftment of a tissue graft, wherein the method comprises: providing a composition comprising ruptured mitochondria; and administering the composition to a subject engrafted with the tissue graft. According to yet another embodiment, the present invention provides a method for enhancing engraftment of a tissue graft, wherein the method comprises: providing a composition comprising partially purified intact mitochondria, wherein said partially purified intact mitochondria have undergone at least one freeze-thaw cycle; and administering the composition to a subject engrafted with the tissue graft.

According to yet another embodiment, the present invention provides a method for enhancing engraftment of a tissue graft, wherein the method comprises: providing a composition comprising mitochondria; and administering the composition to a subject engrafted with the tissue graft.

According to some embodiments, the term "engraftment", as used herein, refers to incorporation of grafted tissue into the body of the host. The importance of sufficient blood supply in a graft for a successful engraftment is known in the art.

According to some embodiments, the term "tissue graft", as used herein, refers to a tissue from a donor that is used to replace missing or damaged tissue in a subject. According to some embodiments, the tissue graft is syngeneic, allogeneic or xenogeneic, each possibility representing a separate embodiment of the present invention. According to some embodiments, the tissue graft is a skin graft, a vascular graft, a bone graft, a corneal graft, a ligament graft, an engineered tissue or a combination thereof. Each possibility represents a separate embodiment of the present invention.

According to some embodiments, enhancing is inducing angiogenesis in the tissue graft. According to some embodiments, enhancing is restoring blood flow to the tissue graft. According to some embodiments, enhancing is preventing rejection of the tissue graft. According to some embodiments, enhancing accelerates the engraftment process. According to some embodiments, enhancing restores blood supply to the tissue graft.

Without wishing to be bound by any theory or mechanism, administration of the composition to the tissue graft results in an accelerated formation of vasculature. The vasculature supplies blood to the tissue graft, enabling accelerated and improved engraftment.

According to some embodiments, administering is injecting into the tissue graft. According to some embodiments, administering is injecting into the site of engraftment. According to some embodiments, administering is injecting systemically. According to some embodiments, administering is topically administering to the tissue graft. According to some embodiments, administering is topically administering to the site of engraftment.

As used herein, the expression "site of engraftment" refers to a site in which there is damaged or missing tissue.

In one embodiment, toxicity and therapeutic efficacy of the preparation described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition.

According to another aspect, the present invention provides a composition comprising partially purified intact mitochondria and/or ruptured mitochondria derived therefrom for use in inducing angiogenesis in a tissue; wherein said partially purified intact mitochondria have undergone at least one freeze-thaw cycle. Each possibility represents a separate embodiment of the present invention. According to some embodiments, the present invention provides a composition comprising partially purified intact mitochondria for use in inducing angiogenesis in a tissue; wherein said partially purified intact mitochondria have undergone at least one freeze-thaw cycle. According to some embodiments, the present invention provides a composition comprising ruptured mitochondria for use in inducing angiogenesis in a tissue. According to some embodiments, the present invention provides a composition comprising partially purified intact mitochondria and ruptured mitochondria for use in inducing angiogenesis in a tissue; wherein said partially purified intact mitochondria have undergone at least one freeze-thaw cycle. According to some embodiments, the present invention provides use of a composition comprising partially purified intact mitochondria and/or ruptured mitochondria derived therefrom for preparation of a medicament for inducing angiogenesis in a tissue. Each possibility represents a separate embodiment of the present invention.

According to another aspect, the present invention provides a composition comprising partially purified intact mitochondria and/or ruptured mitochondria derived therefrom for use in treating a subject afflicted with a pathology which would benefit from angiogenesis; wherein said partially purified intact mitochondria have undergone at least one freeze-thaw cycle. Each possibility represents a separate embodiment of the present invention. According to some embodiments, the present invention provides a composition comprising partially purified intact mitochondria for use in treating a subject afflicted with a pathology which would benefit from angiogenesis; wherein said partially purified intact mitochondria have undergone at least one freeze-thaw cycle. According to some embodiments, the present invention provides a composition comprising ruptured mitochondria for use in treating a subject afflicted with a pathology which would benefit from angiogenesis. According to some embodiments, the present invention provides a composition comprising partially purified intact mitochondria and ruptured mitochondria for use in treating a subject afflicted with a pathology which would benefit from angiogenesis; wherein said partially purified intact mitochondria have undergone at least one freeze-thaw cycle. According to some embodiments, the present invention provides a use of a composition for preparation of a medicament for treating a subject afflicted with a pathology which would benefit from angiogenesis, the composition comprising partially purified intact mitochondria and/or ruptured mitochondria derived therefrom. Each possibility represents a separate embodiment of the present invention.

According to another aspect, the present invention provides a composition comprising partially purified intact mitochondria and/or ruptured mitochondria derived therefrom for use in enhancing engraftment of a tissue graft; wherein said partially purified intact mitochondria have undergone at least one freeze-thaw cycle. Each possibility represents a separate embodiment of the present invention. According to some embodiments, the present invention provides a composition comprising partially purified intact mitochondria for use in enhancing engraftment of a tissue graft; wherein said partially purified intact mitochondria have undergone at least one freeze-thaw cycle. According to some embodiments, the present invention provides a composition comprising ruptured mitochondria for use in enhancing engraftment of a tissue graft. According to some embodiments, the present invention provides a composition comprising partially purified intact mitochondria and ruptured mitochondria for use in enhancing engraftment of a tissue graft; wherein said partially purified intact mitochondria have undergone at least one freeze-thaw cycle. According to some embodiments, the present invention provides a use of a composition for preparation of a medicament for enhancing engraftment of a tissue graft, the composition comprising partially purified intact mitochondria and/or ruptured mitochondria derived therefrom. Each possibility represents a separate embodiment of the present invention.

According to some embodiments, the present invention provides a kit for inducing angiogenesis in a tissue, the kit comprising a composition comprising partially purified intact mitochondria and/or ruptured mitochondria derived therefrom and instructions for using the kit for inducing angiogenesis in a tissue. Each possibility represents a separate embodiment of the present invention. According to some embodiments, the present invention provides a kit for treating a subject afflicted with a pathology which would benefit from angiogenesis, the kit comprising a composition comprising partially purified intact mitochondria and/or ruptured mitochondria derived therefrom and instructions for using the kit for treating a subject afflicted with a pathology which would benefit from angiogenesis. Each possibility represents a separate embodiment of the present invention. According to some embodiments, the present invention provides a kit for enhancing engraftment of a tissue graft, the kit comprising a composition comprising partially purified intact mitochondria and/or ruptured mitochondria derived therefrom and instructions for using the kit for enhancing engraftment of a tissue graft. Each possibility represents a separate embodiment of the present invention.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Mitochondria that were Frozen and Thawed Show Oxygen Consumption Comparable to that of Non-Frozen Mitochondria Mitochondria were isolated from mouse term placenta according to the following protocol:
1. Placenta was rinsed free of blood by using ice-cold TB buffer (isolation buffer: 200 mM sucrose, 1 mM EGTA and 10 mM Tris-MOPS)+0.2% BSA.
2. The placenta was minced into small pieces in 5 ml IB+0.2% BSA using scissors.
3. The suspension was transferred to a 10 ml glass potter and homogenized using a Dounce glass homogenizer by five complete up and down cycles.
4. The homogenate was transferred to a 15 ml tube and centrifuged at 600 g for 10 min at 4° C.
5. The supernatant was transferred to clean centrifuge tubes and the pellet was resuspended in IB buffer, and subjected to a second centrifugation step.
6. The supernatant from steps 4 and 5 was filtered through a 5 µm filter to remove any cells or large cell debris.

7. The supernatant was recovered and centrifuged at 7,000×g for 15 min.
8. The mitochondrial pellet was washed in 10 ml ice cold IB buffer and mitochondria were recovered by centrifugation at 7,000×g for 15 min at 4° C.
9. The supernatant was discarded and the pellet resuspended, containing mitochondria in 200 µl of IB buffer.
10. Protein content was determined by the Bradford assay.

To compare activity of frozen versus unfrozen mitochondria, mitochondria were flash-frozen using liquid nitrogen in IB (200 mM sucrose, 1 mM EGTA and 10 mM Tris-MOPS) in 1.5 ml Eppendorf tubes and kept at −70° C. for 30 minutes. Mitochondria were thawed quickly by hand and $O_2$ consumption by 100 µg mitochondria was measured using the MitoXpress fluorescence probe (Luxcel) and a Tecan plate reader. Oxygen consumption was measured in the presence of 25 mM Succinate (S) or in the presence of 25 mM Succinate and 1.65 mM ADP (S+ADP). The change in fluorescence was calculated relative to the level of fluorescence at time 0. FIG. 1 shows that the $O_2$ consumption, and rate of $O_2$ consumption, were comparable for mitochondria that were frozen and thawed (marked "Frozen") in comparison to non-frozen mitochondria (marked "Fresh").

As opposed to frozen mitochondria, mouse placental mitochondria that were chilled (kept for 4 days at 4° C.) produced less ATP than fresh mitochondria (Table 1).

TABLE 1

ATP production of fresh and chilled mouse placental mitochondria

|  | ATP (RLU) |
|---|---|
| Fresh Mitochondria (F) | 4690 |
| Chilled Mitochondria (C) | 1587 |

Example 2

Figure 2:
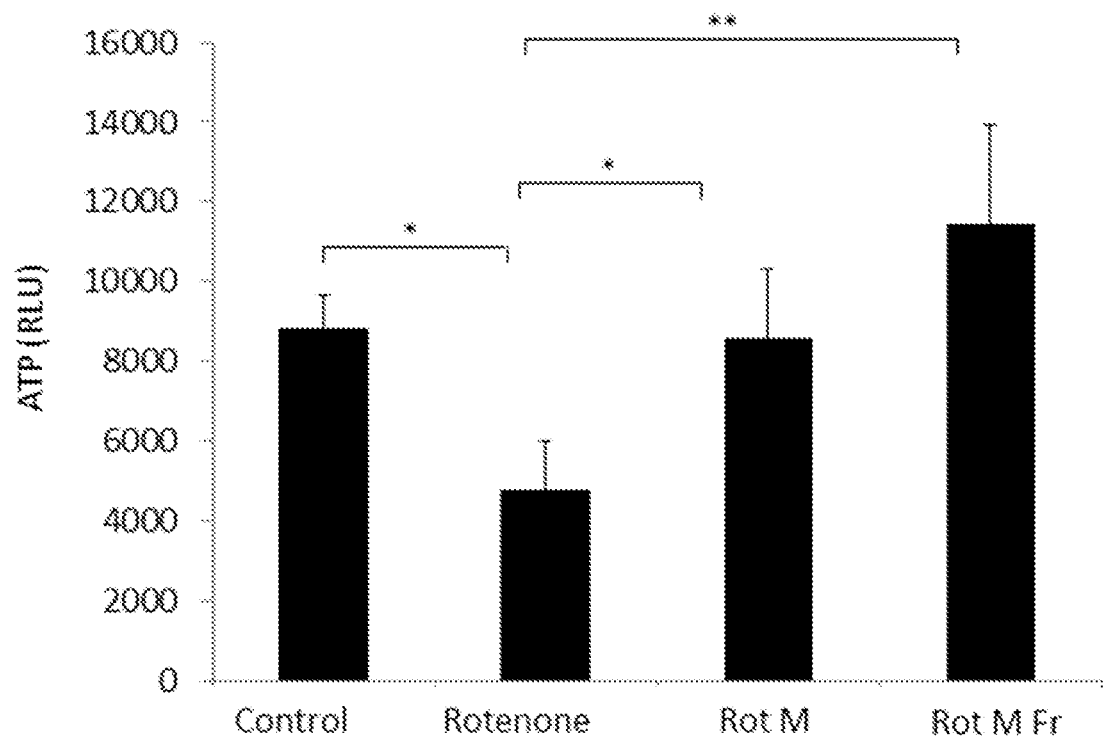
FIG. 2 is a bar graph showing the effect of fresh versus frozen mitochondria on ATP level in 3T3-L1 cells that were treated for 4 h with the mitochondrial complex I inhibitor Rotenone.

Mouse 3T3-L1 Cells Treated with Mitochondria that were Frozen and Thawed Show Higher Rescue of Rotenone-Induced Mitochondrial Inhibition Mouse 3T3-L1 cells (30,000 cells) were either untreated (Control) or incubated with the mitochondrial complex I inhibitor Rotenone (0.5 µM) for 4 hours. Following incubation cells were washed and either left untreated (Rotenone), treated with fresh mouse placental mitochondria (Rot M) or treated with 2 µg of mouse placental mitochondria that were frozen and thawed (Rot M Fr) for 24 h in 50 µl medium. Mitochondria activity was assayed by measuring ATP production using ATPlight by Perkin-Elmer. As can be seen in FIG. 2, cells that were treated with frozen mitochondria show rescue of Rotenone-inhibited ATP production at least to the same extent as cells that were treated with fresh mitochondria, suggesting that frozen mitochondria are at least as functional as fresh mitochondria (*—$p<0.01$, **—$p<0.05$).

Example 3

3T3-L1 Cells Incubated with Placental Mitochondria Show Increased Citrate Synthase Activity and ATP Production Mitochondria were isolated from mouse term placenta, bovine placenta or human placentas according to the protocol described in example 1.

Figure 3A:
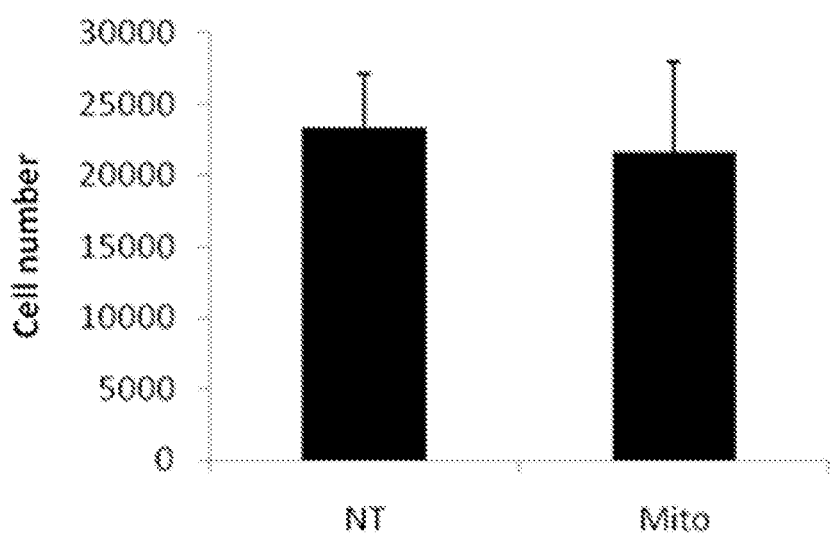
FIGS. 3A-C are bar graphs showing a comparison of cell number (FIG. 3A), ATP contents (FIG. 3B) and citrate synthase (CS) activity (FIG. 3C) between 3T3-L1 cells enriched with bovine placental mitochondria (Mito) and control cells (NT).
Figure 3B:
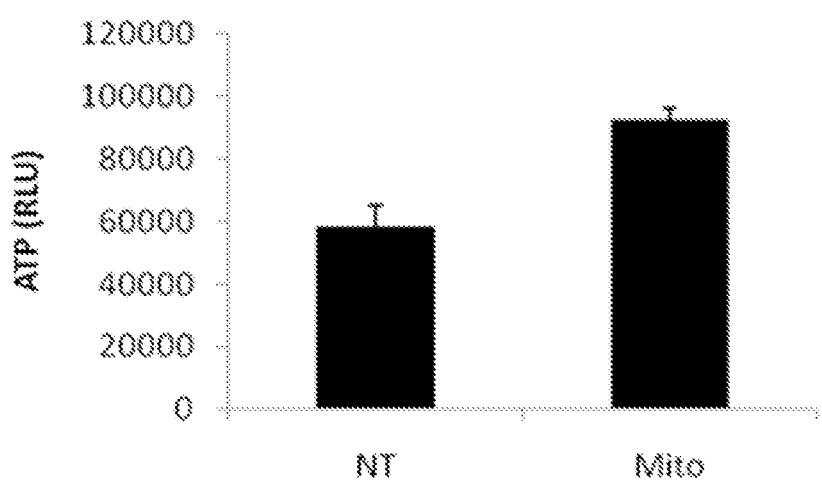
Figure 3C:
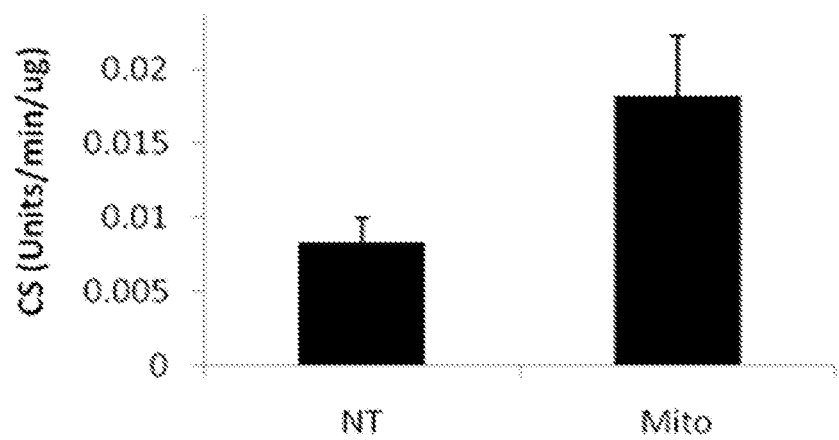

3T3-L1 cells were cultured in 24 wells plates until confluent and subsequently incubated with 20 µg of mitochondria in 200 µl of growing media (DMEM+10% Bovine serum) for 24 hours. The cells were washed in PBS, trypsinized and transferred to 4 wells of 24 wells plate. Twenty four hours later the cells were washed in PBS, trypsinized and counted. 3T3-L1 cells, which were not incubated with the mitochondria preparation described above, were used as control cells (not treated, NT). As depicted in FIG. 3A, no significant difference was observed between the number of cells grown comprising the exogenous mitochondria (Mito) and control cells (NT). However, ATP content, measured using ATPlight by Perkin-Elmer, was significantly increased in the Mito cells as compared to control (FIG. 3B). In addition, the level of citrate synthase activity, measured using the citrate synthase assay kit by Sigma, was significantly increased in the Mito cells as compared to control cells (FIG. 3C).

Example 4

Figure 4A:
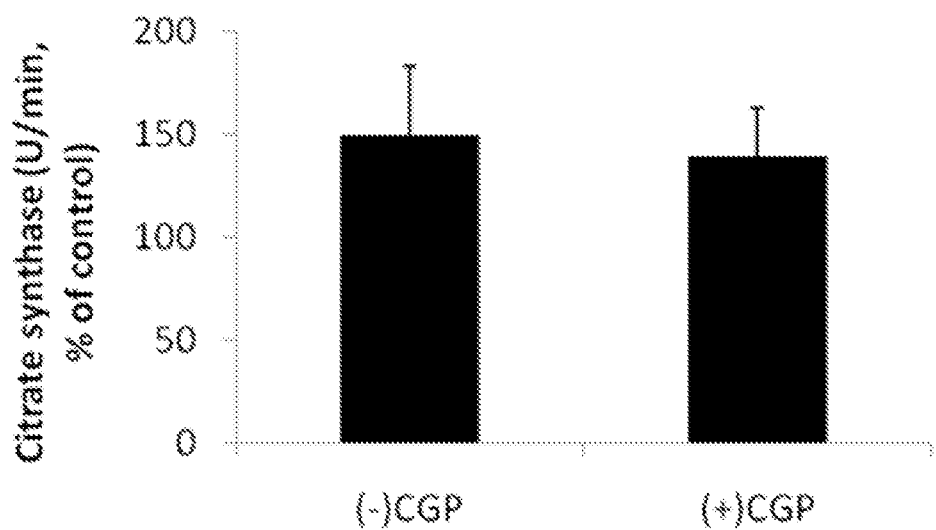
FIGS. 4A-B are bar graphs showing citrate synthase activity (A) and ATP level (B) in bEND-3 endothelial cells treated with mitochondria pre-incubated with or without the ion-exchanger inhibitor CGP37157 (CGP).
Figure 4B:
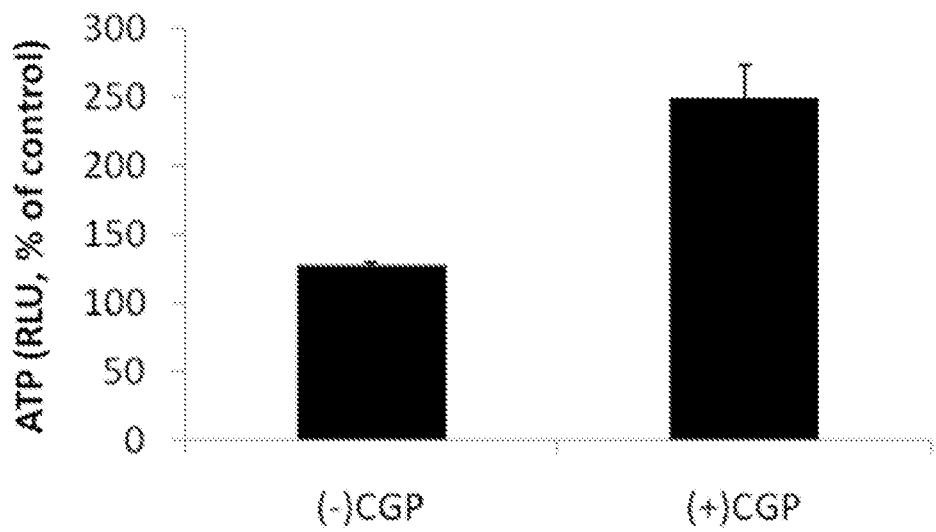

Increased ATP Activity in Endothelial Cells Incubated with CGP37157-Treated Mitochondria Mitochondria were isolated from 400 mg bovine term placenta according to the protocol described in Example 1. At step 2, the placenta was minced in the presence or absence of CGP37157 (Sigma®), a mitochondrial $Na^+/Ca^+$ exchanger blocker. Brain mouse endothelial cells (bEND3) were cultured in 24 wells plates until confluent. Cells were left untreated or incubated with 18 µg of the above described mitochondria preparation in 200 µl of DMEM+10% fetal bovine serum for 24 hours. As a control, cells were incubated with a mitochondria preparation which was not treated with CGP37157. Cells were then washed in PBS, trypsinized and cultured for an additional 24 hours. The cells were then trypsinized and as shown in FIG. 4A, no difference was observed between the level of citrate synthase activity between cells comprising exogenous mitochondria treated with CGP37157 ((+) CGP) as compared to cells comprising exogenous mitochondria untreated with CGP37157 ((−) CGP). However, as shown in FIG. 4B, the ATP level was significantly increased in cells comprising exogenous mitochondria which were pretreated with CGP37157 ((+) CGP) in the isolation process, as compared to control cells ((−) CGP). The data in FIGS. 4A and 4B are presented as percentage of the non-treated cells.

Example 5

Figure 5A:
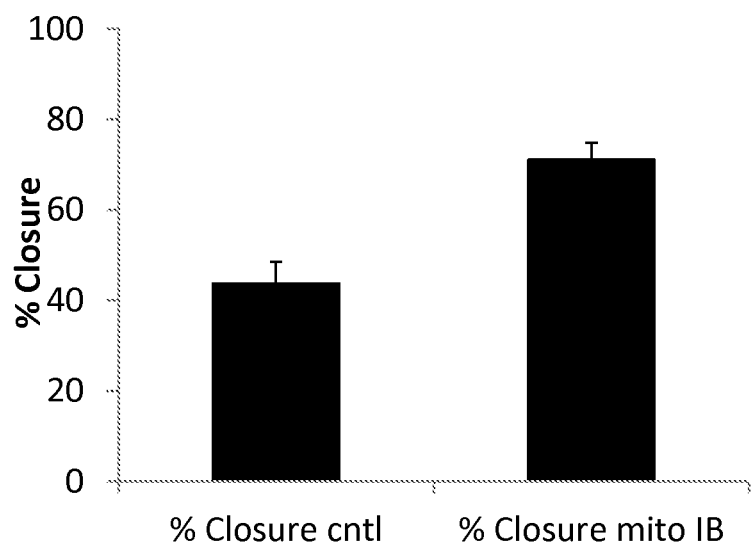
FIGS. 5A-B include graphs showing that a mitochondrial treatment of the invention induces cell proliferation and cell migration in a scratch assay. Endothelial cell migration was measured as a percentage of scratch closure (FIG. 5A), whereas cell proliferation was assayed by measuring the ATP level using the LONZA ViaLight ATP kit (FIG. 5B).
Figure 5B:
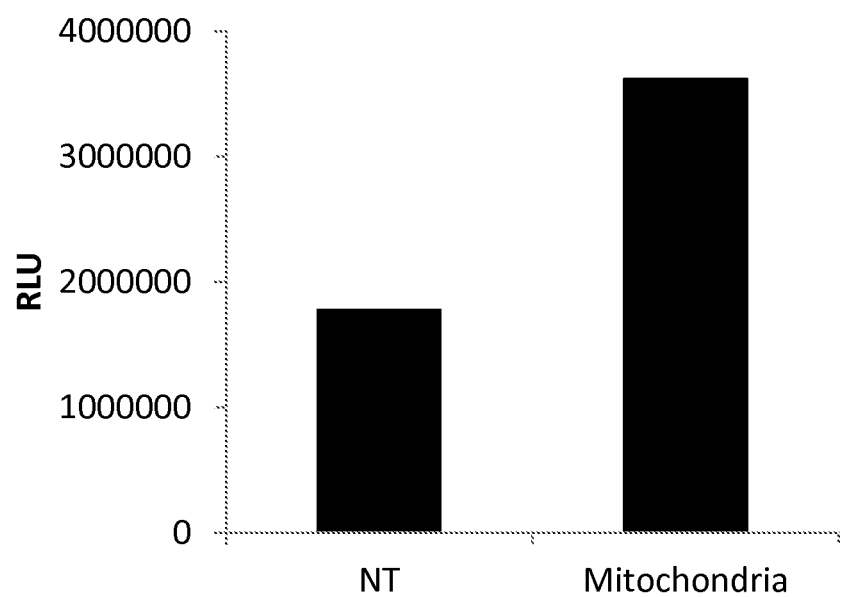

Mitochondria Induce the Proliferation and/or Migration of Mouse Endothelial Cells About 300,000 brain mouse-derived endothelial cells (bEND3) were plated in 35 mm dishes until confluent. The cells were scratched using a 200 µl tip and were either non-treated or treated with 20 µg mouse placental mitochondria in isolation buffer (mito IB). Following 24 hours incubation, the width of the scratch was measured and the percentage of closure was calculated. FIG. 5A demonstrates an increased closure percentage in a scratch treated with mitochondria (Closure mito IB) as compared to a non-treated scratch (Closure end). Three days later ATP level in each plate was evaluated using ATPlight by Perkin-Elmer as a measurement of cell number. FIG. 5B demonstrates that cells treated with mitochondria (mitochondria) showed a higher ATP level than untreated cells (NT), indicating a higher cell number. These results demonstrate that the mitochondria treatment of the invention may induce cellular proliferation and/or cellular migration. These processes are highly important in induction of angiogenesis and for the treatment of pathologies such as ischemia and CLI.

Example 6

Mitochondria Induce Proliferation of Mouse Endothelial Cells

Figure 6:
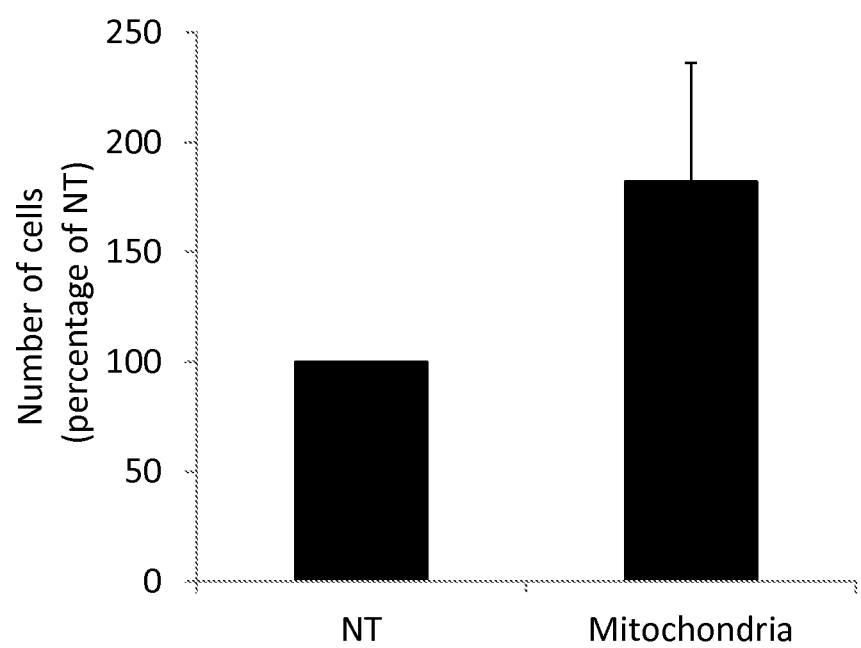
FIG. 6 is a bar graph showing that mitochondria isolated from mouse term placenta induce proliferation/mitosis of bEND3 mouse endothelial cells.

Mouse endothelial cells (bEND3, ATCC) were seeded in a 24-well plate at a concentration of 60,000 cells per well. Mitochondria were isolated from mouse term placenta and incubated with the cells, 5 µg mitochondria/200 µl medium. Twenty four hours later the medium was changed and the following day the cells were trypsinized and counted. FIG. 6 shows that the mitochondria treatment induces proliferation of bEND3 cells as shown by the number of cells 48 hours after placental mitochondria treatment (mitochondria) as compared to untreated cells (NT).

Example 7

Mitochondria Induce Ex-Vivo Angiogenesis

Figure 7A:
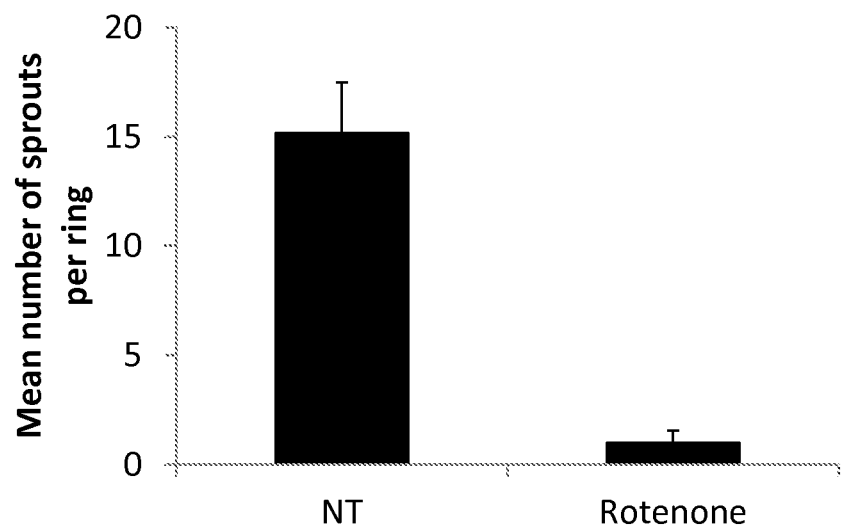
FIGS. 7A-B are bar graphs showing the effect of exogenous mitochondria on sprouting of mouse aortic rings. The mitochondrial complex I inhibitor Rotenone blocked sprouting almost completely (FIG. 7A), while pre-treatment with mouse placental mitochondria increased the sprouting of new blood vessels from embedded aortic rings (FIG. 7B).
Figure 7B:
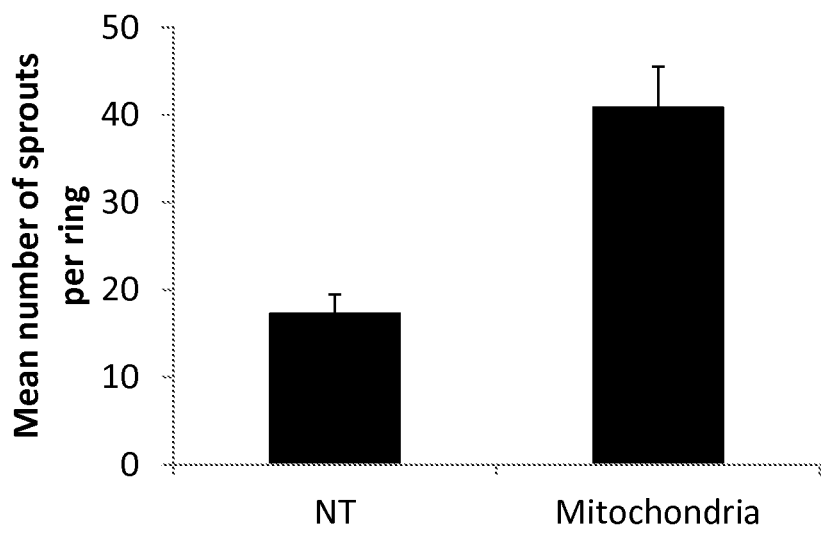

Thoracic aorta were removed from female C57/BL mice and cut into 0.5 mm rings. Aortic rings were incubated in serum-free medium and either left untreated or treated with 0.5 µM Rotenone for 4 hours. To assess mitochondria effect on sprouting of aortic rings, half of the non-treated rings were washed and incubated with 25 µg of C57/BL mouse placental mitochondria in 2 ml serum-free medium. After 24 hours the rings were embedded in rat tail collagen, one ring per well in a 96 wells plate. After 8 days in culture the level of sprouting was evaluated by counting the number of vessels per ring. FIGS. 7A-C show the number of blood vessels sprouting from mouse aortic rings that were embedded in collagen matrix. The mitochondrial complex I inhibitor Rotenone blocked the sprouting almost completely (FIG. 7A), while pre-treatment with mouse placental mitochondria increased the sprouting of new blood vessels from the embedded aortic rings (FIG. 7B). Buerger's disease and CLI patients suffer from sever obstruction of the arteries which leads to decreased blood flow in the limbs. Sprouting of blood vessels requires proliferation of endothelial cell. FIGS. 5 and 6 show that mitochondrial-treatment can induce the proliferation of endothelial cells in a 2D culture system. FIGS. 7A-C show that mitochondria play a critical role in the sprouting of new blood vessels in a 3D aortic rings model and that treatment of rings with exogenous placental mitochondria dramatically induces the formation of new blood vessels.

Moreover, the current results suggest that exogenous placental mitochondria may be used for the induction of angiogenesis in CLI or other ischemic conditions. The results show that exogenous mitochondria act by both increasing the level of extracellular ATP and by increasing the mitochondrial activity inside the cells. Both processes are essential for proper angiogenesis.

Example 8

Induction of In-Vitro Angiogenesis by Mitochondria and VEGF

Figure 8:
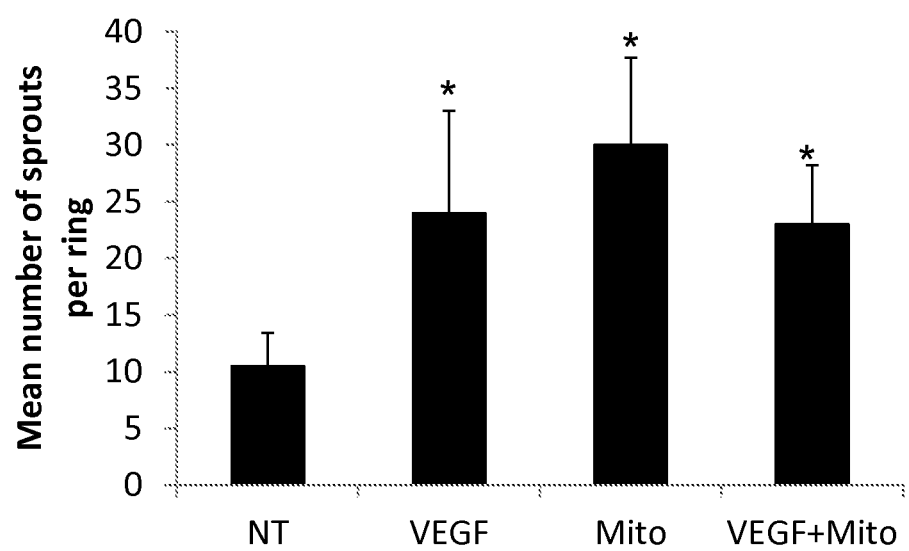
FIG. 8 is a bar graph comparing the effect of exogenous mitochondria, VEGF and their combination on sprouting of mouse aortic rings.

The effect of VEGF, mitochondria and mitochondria+ VEGF on sprouting of aortic rings in-vitro was examined Mouse aortic rings were prepared as described in example 7 and were either left un-treated (NT), treated with 25 µg mouse placental mitochondria in 2 ml OptiMem medium for 24 h (Mito), incubated in OptiMem medium containing 2.5% FBS and 30 ng/ml mouse VEGF for 48 h (VEGF) or treated with both mitochondria and VEGF (VEGF+Mito). The number of new blood vessels sprouting from the aortic rings was counted on day 8. As can be seen in FIG. 8, no significant difference was observed in ring number between the VEGF, Mito or VEGF+Mito groups (*—p<0.05).

Example 9

Dose-Dependent Induction of Ex-Vivo Angiogenesis by Mitochondria

Figure 9:
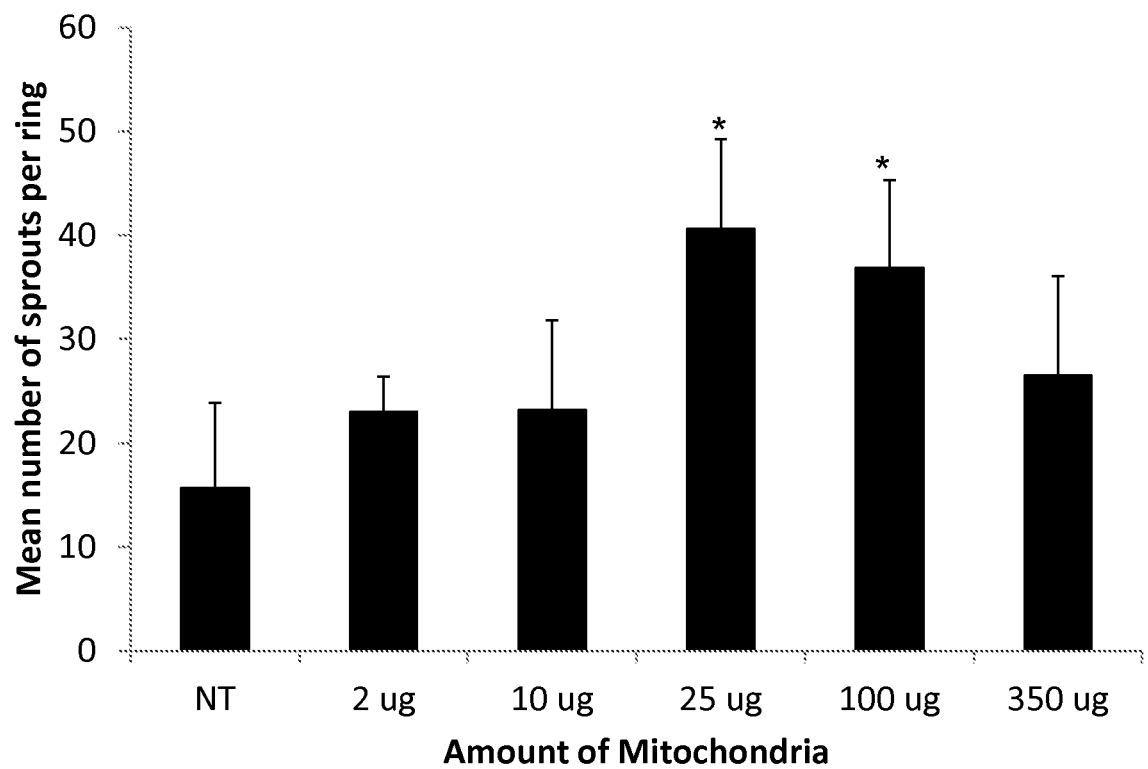
FIG. 9 is a bar graph comparing the effect of increasing concentrations of exogenous mitochondria on sprouting of mouse aortic rings.

A dose-dependent effect of mitochondria on the number of blood vessels was evaluated in a mouse aortic ring model. Mouse aortic rings were prepared as described in example 7 and were either left un-treated or treated with increasing amounts (2-350 µg) of mouse placental mitochondria in 2 ml OptiMem medium for 24 h. The number of new blood vessels sprouting from the aortic rings was counted on day 7. As can be seen in FIG. 9, increasing the amount of mitochondria resulted in an increase in the number of sprouts, with the highest number of sprouts observed upon addition of 25 µg and 100 µg of mitochondria in 2 ml OptiMem medium (*—p<0.05).

Example 10

Figure 10A:
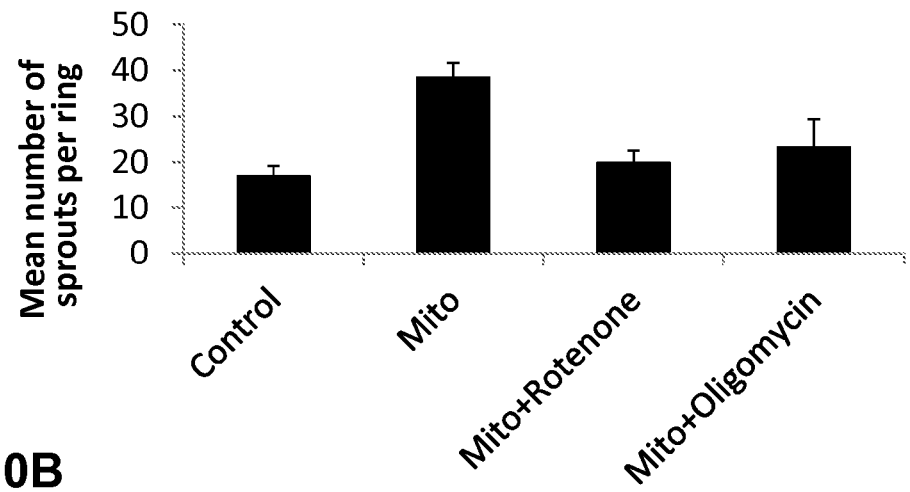
FIGS. 10A-D includes a bar graph (FIG. 10A) comparing the effect of exogenous mitochondria with or without the inhibitors Rotenone or Oligomycin, on the mean number of sprouts per aortic ring, and dot-plots (FIGS. 10B-D) showing mitochondrial function over time, with or without each of the inhibitors, Rotenone or Oligomycin.

Induction of Ex-Vivo Angiogenesis by Mitochondria with or without Inhibitors Rotenone or Oligomycin The effect of mitochondria on the number of blood vessels was evaluated in a mouse aortic ring model. Mouse aortic rings were prepared as described in example 7 and were either left un-treated (Control), treated for 24 h with 25 µg of mouse placental mitochondria (Mito), treated with mitochondria that were inhibited by 2 µM of mitochondria complex I inhibitor Rotenone or treated with mitochondria that were inhibited with 5 µM of the ATP Synthase inhibitor Oligomycin for 24 h. The number of new blood vessels sprouting from the aortic rings was counted on day 8. As can be seen in FIG. 10A, mitochondria that were treated with Rotenone or Oligomycin induced less sprouts than mitochondria that were untreated (P<0.00001).

Figure 10B:
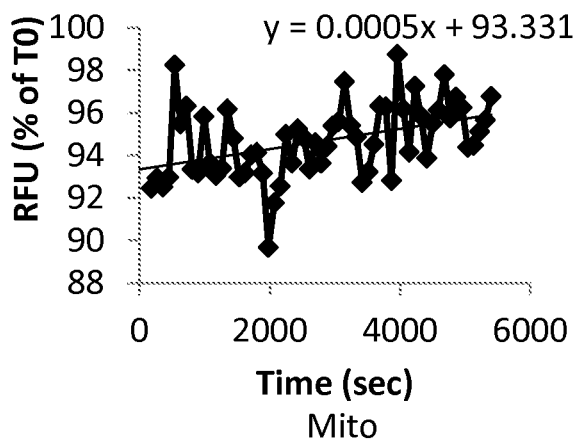
Figure 10C:
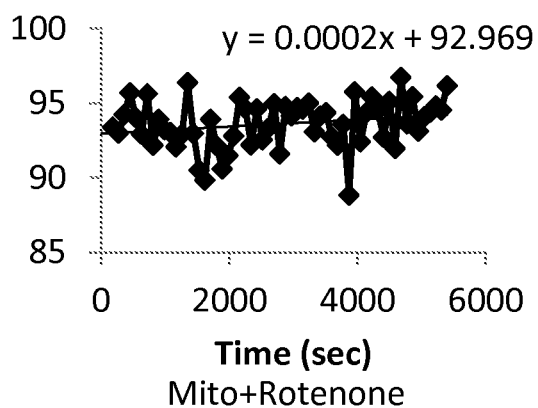
Figure 10D:
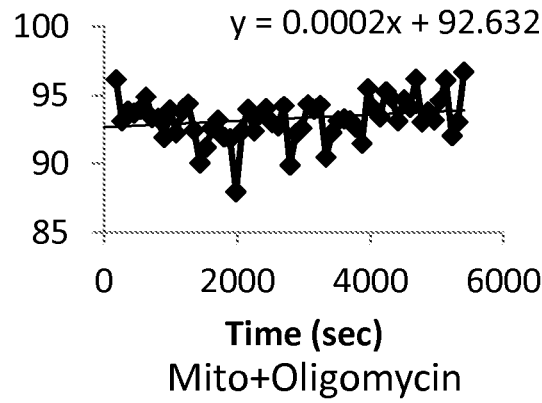

Mitochondrial function over time was measured as a function of mitochondrial respiration by the MitoXpress fluorescence probe (Luxcel), using 25 µg of mitochondria. As can be seen in FIG. 10B-D, mitochondrial function over time was decreased in mitochondria treated by Rotenone or Oligomycin, as compared to untreated mitochondria (P<0.05). The results presented in FIG. 10 suggest that the ability of mouse placental mitochondria to induce sprouting of blood vessels from aortic rings depends on mitochondrial activity.

Example 11

Mitochondria Induce Recovery of Blood Flow in Hind Limb Ischemia (HLI) Mouse Model Stable severe hind limb ischemia mouse model was applied to assess mitochondrial suspension as an angiogenesis inducer after local intramuscular administration. The femoral artery of 9 weeks old Balb/c male mice was ligated twice with 6-0 silk thread and transected between the ligatures. The transection wound was closed using a 4-0 silk thread and the mice were allowed to recover. On day 1, 24 hours post-surgery, each animal received an intramuscular injection of 350 µg mitochondrial suspension (derived from mouse term placentas), suspended in isolation buffer, at two sites: the proximal and the distal side of the surgical wound. A volume of 50 µl was injected at each location arriving at a total volume of 100 µl. Blood flow in hind legs of both sides was measured using a non-contact laser Doppler prior to surgery and on days: 1, 7 14, 21, and 28 post surgery. Blood flow measurements were expressed as the ratio between the flow in the ischemic limb to that in the intact limb.

Figure 11:
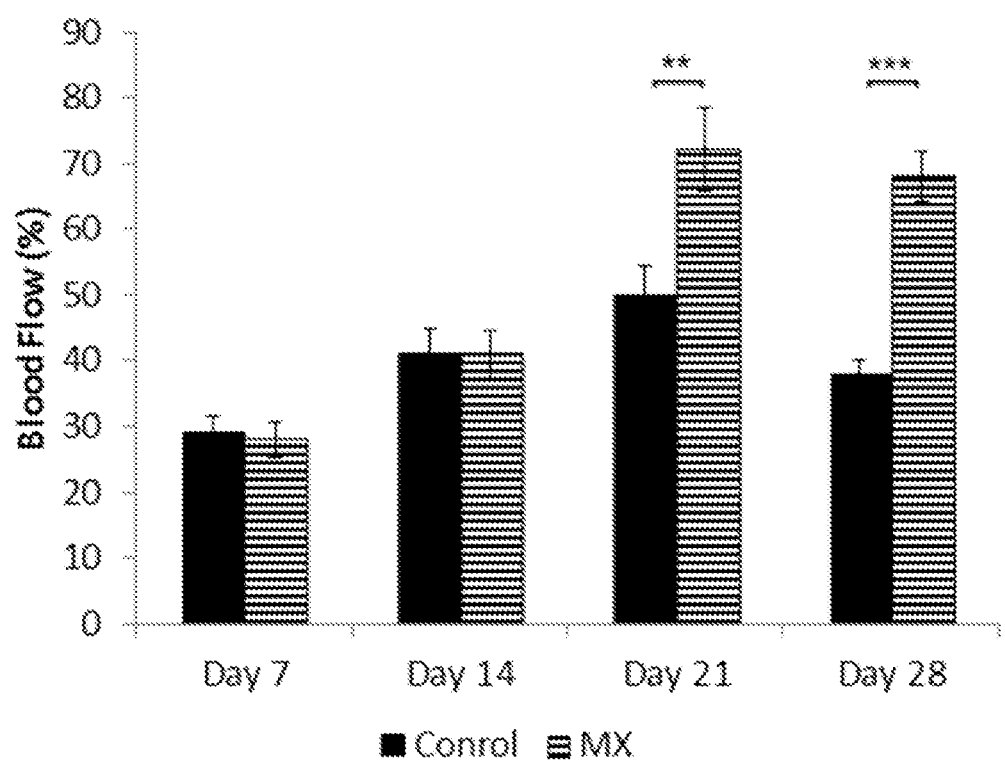
FIG. 11 is a bar graph comparing the blood flow percentage in hind limbs of mice used as a model of severe hind limb ischemia, treated either with a placental mitochondria suspension (MX) or a control vehicle.

As can be seen in FIG. 11, starting at day 21 and up to study termination on day 28, statistically significant improvement (p<0.01-0.001) in hind limb blood flow was observed in the animal group treated with mitochondrial suspension (MX) as compared to vehicle treated control (—p<0.01, *—p<0.001).

Example 12

Mitochondria Suspended in a Buffer Containing a High Sucrose Concentration Show a Higher Oxygen Consumption Placental mouse mitochondria (25 µg) were suspended in isolation buffer (1 mM EGTA, 10 mM Tris-MOPS) containing either 20 mM sucrose (MP) or 200 mM sucrose (M). Oxygen consumption over time was measured using the MitoXpress fluorescence probe (Luxcel) and a Tecan plate reader. The percentage of change in fluorescence was calculated relative to the level of fluorescence at time 0. A trend line was plotted to determine the average change in fluorescence over time which stands for the rate of $O_2$ consumption (the slope of the line).

Figure 12:
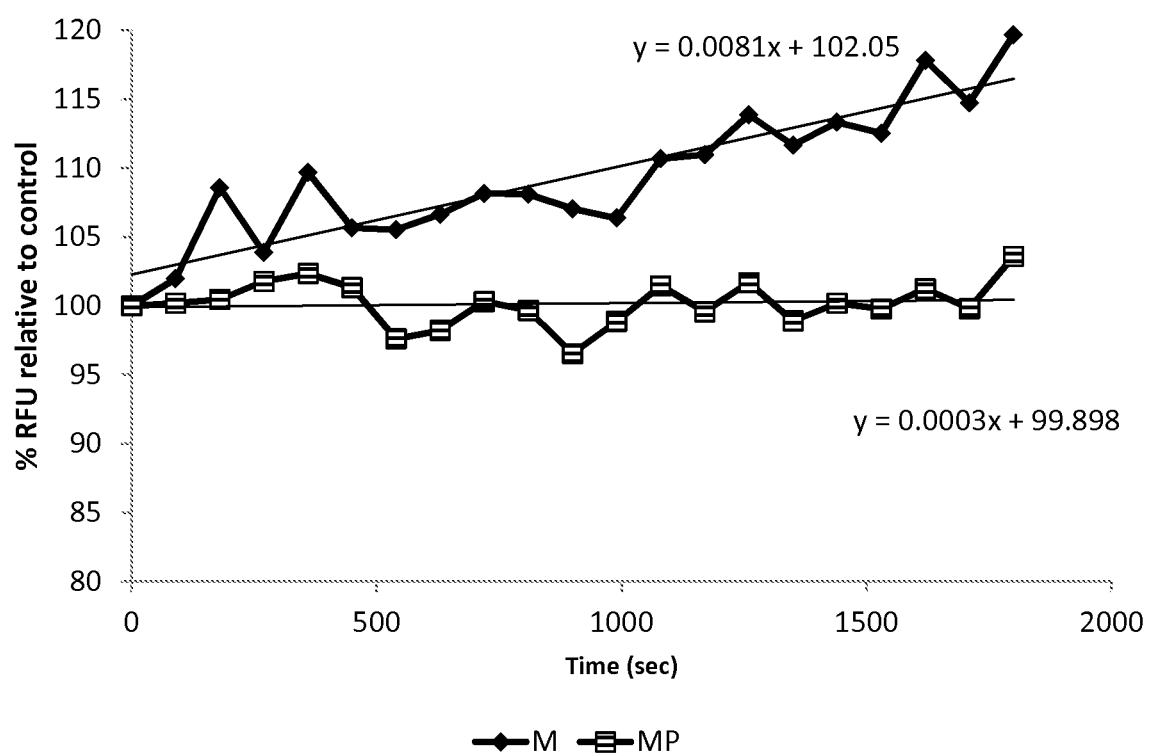
FIG. 12 is a dot-plot showing $O_2$ consumption over time in a mitochondrial composition comprising 20 mM sucrose (MP) or 200 mM sucrose (M).

As can be seen in FIG. 12, the rate of oxygen consumption was higher in mitochondria that were suspended in a buffer containing 200 mM sucrose.

Example 13

Cell Migration of bEND3 Endothelial Cells Treated with Mitochondria Suspended in a Buffer Containing a High Concentration of Sucrose Mouse bEND3 endothelial cells were plated in a 35 mm dish until a confluent monolayer was achieved. The cells were scratched using a 200 µl tip and were either untreated (entl), treated with 20 µg mouse placental mitochondria suspended in an isolation medium comprising sucrose (200 mM, 1 mM EGTA, 10 mM Tris-MOPS) (IB) or treated with 20 µg mouse placental mitochondria suspended in PBS (PBS). Cell migration was determined as a function of scratch closure percentage after incubation of 24 hours.

Figure 13:
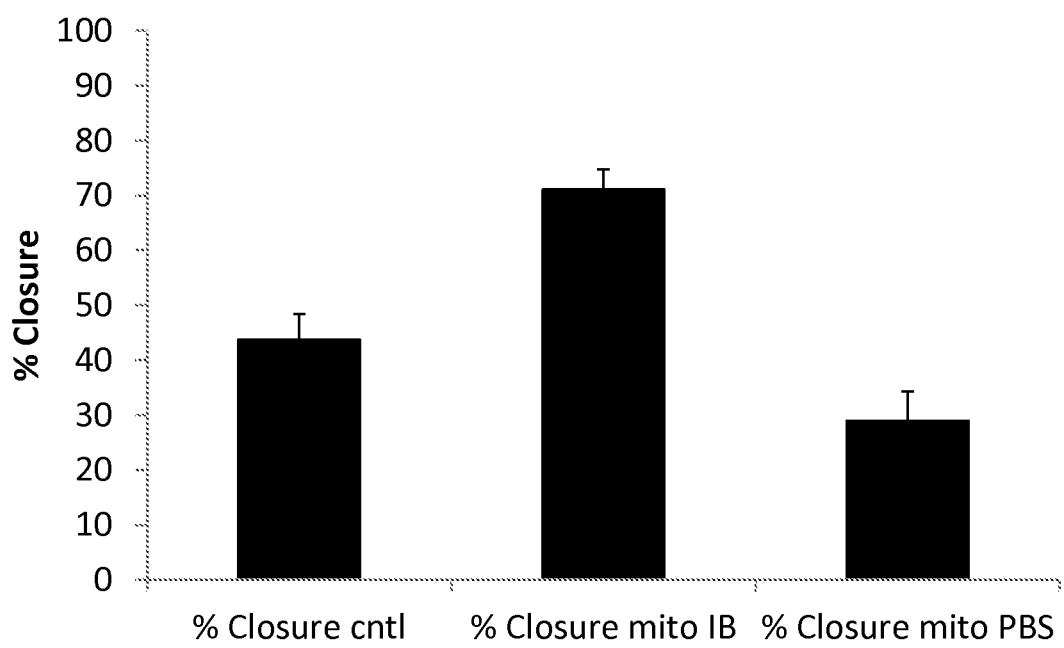
FIG. 13 is a bar graph comparing cell migration in a scratch assay of cells that were either untreated (entl), treated with mitochondria suspended in a buffer comprising 200 mM sucrose (IB) or treated with mitochondria suspended in PBS (PBS).

As can be seen in FIG. 13, only mitochondria that were suspended in the sucrose-containing isolation buffer were able to induce closure to a higher degree than the control cells.

Example 14

Dose Calibration of Mitochondria-Induced Angiogenesis in a Mouse Hind-Limb Ischemia Model Stable severe hind limb ischemia mouse model was applied to compare the angiogenesis-induction ability of different doses of mitochondrial compositions. The femoral arteries of 9 weeks old Blab/c male mice were ligated twice with 6-0 silk thread and transected between the ligatures. The transection wound was closed using a 4-0 silk thread and the mice were allowed to recover. On day 1, 24 hours post-surgery, each animal received an intramuscular injection of either isolation buffer (IB) or 3.5, 35 or 350 µg of mitochondrial composition (derived from human term placentas according to the method presented in Example 1). The intramuscular injection was performed at two sites—the proximal and the distal side of the surgical wound. A volume of 50 µl was injected at each location arriving at a total volume of 100 µl.

Figure 14:
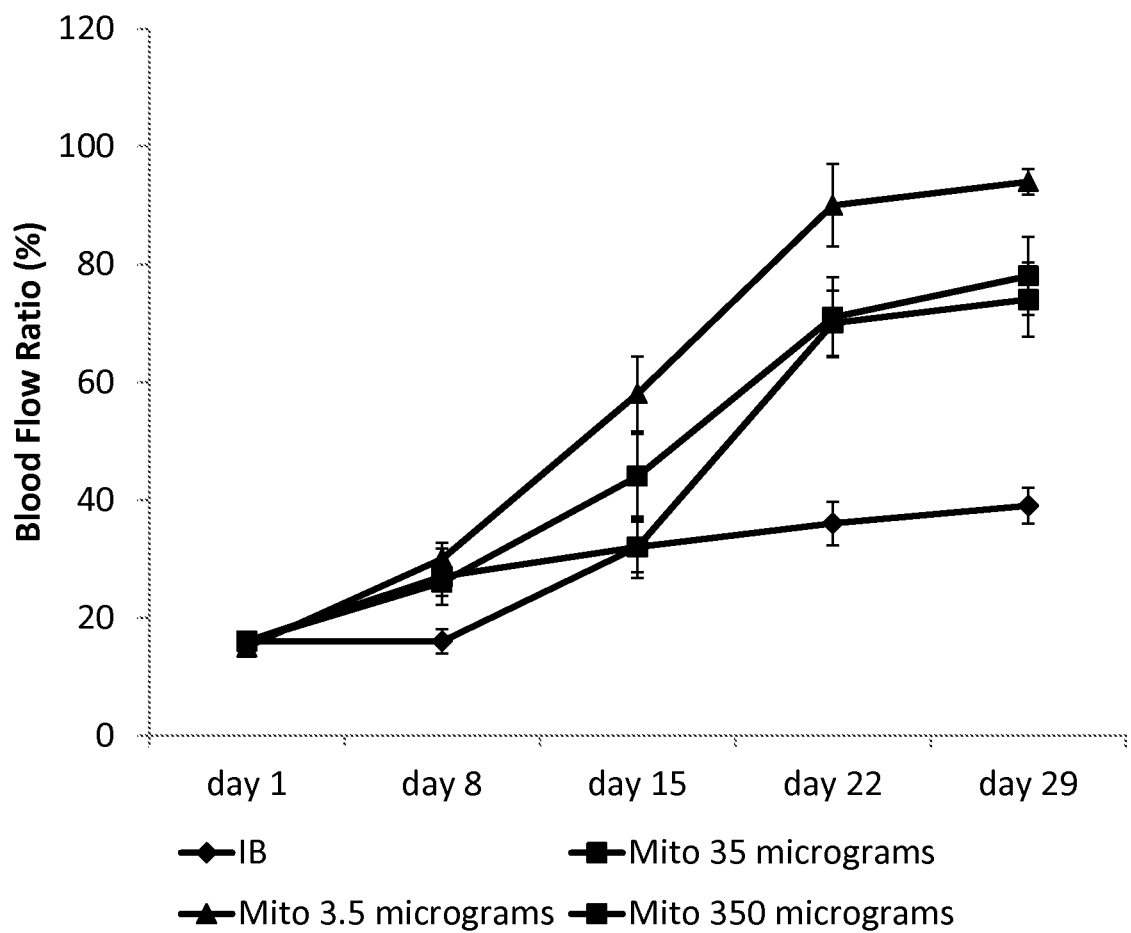
FIG. 14 is a dot plot comparing blood flow ratios resulting from treatment of mouse hind-limb ischemia with increasing doses of mouse placental mitochondria or with isolation buffer (IB).

Blood flow in hind legs of both sides was measured using a non-contact laser Doppler prior to surgery and on days: 1, 7 14, 21, and 28 post surgery. Blood flow measurements were expressed as the ratio between the flow in the ischemic limb and the intact limb. As can be seen in FIG. 14, the highest blood flow ratio was observed following administration of 3.5 µg of the mitochondrial composition.

Example 15

Comparison of Angiogenesis Induced by Mitochondria Suspended in Isolation Buffer or PBS in a Mouse Hind-Limb Ischemia Model Stable severe hind limb ischemia mouse model was applied to compare the angiogenesis-induction ability of mitochondria suspended in isolation buffer (IB) or a hypotonic buffer (PBS). The isolation buffer used contained 200 mM sucrose, 1 mM EGTA and 10 mM Tris-MOPS.

The femoral arteries of 9 weeks old Blab/c male mice were ligated twice with 6-0 silk thread and transected between the ligatures. The transection wound was closed using a 4-0 silk thread and the mice were allowed to recover. On day 1, 24 hours post-surgery, each animal received an intramuscular injection of either IB, PBS, 3.5 µg of mitochondria suspended in IB or 3.5 µg of mitochondria suspended in PBS. The mitochondria used in the experiment were derived from mouse term placentas according to the method presented in Example 1. The intramuscular injection was performed at two sites—the proximal and the distal side of the surgical wound. A volume of 50 µl was injected at each location arriving at a total volume of 100 µl.

Figure 15:
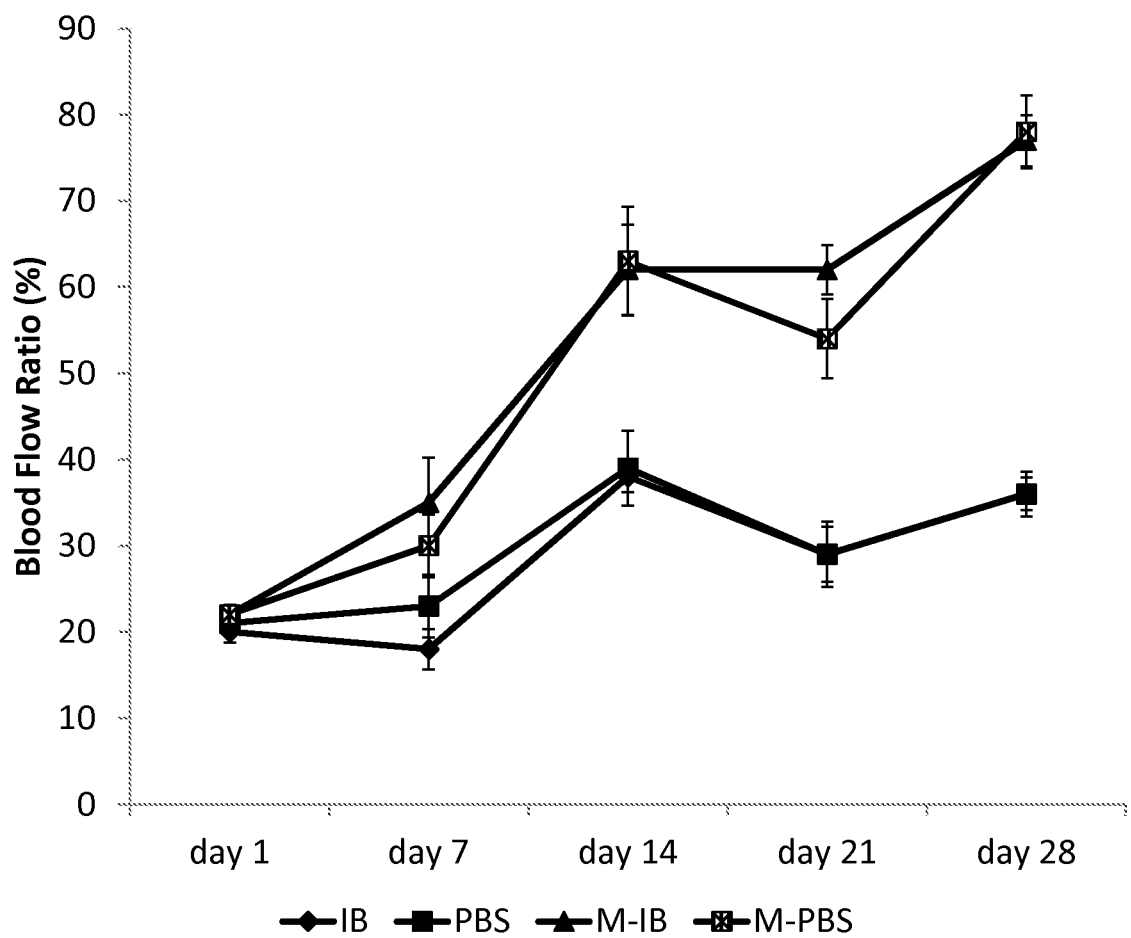
FIG. 15 is a dot plot comparing blood flow ratios resulting from treatment of mouse hind-limb ischemia with mitochondria suspended in either isolation buffer (M-IB), mitochondria suspended in phosphate buffered saline (M-PBS), isolation buffer (IB) or PBS (PBS).

Blood flow in hind legs of both sides was measured using a non-contact laser Doppler prior to surgery and on days: 1, 7 14, 21, and 28 post surgery. Blood flow measurements were expressed as the ratio between the flow in the ischemic limb and the intact limb. As can be seen in FIG. 15, both mitochondrial compositions demonstrated comparable blood flow ratio, suggesting a comparable angiogenesis-induction ability.

Example 16

Capillary Density in Muscles of a Mouse Hind-Limb Ischemia Model Treated with Mitochondria Hind-limb muscles were extracted from the mice described in Example 15, 28 days post-surgery. Four muscle-sections from each of the following groups were scored for capillary density: mice injected with mitochondria in isolation buffer (Mito-IB), mice injected with mitochondria in PBS (Mito-PBS) and untreated mice (NT).

Figure 16:
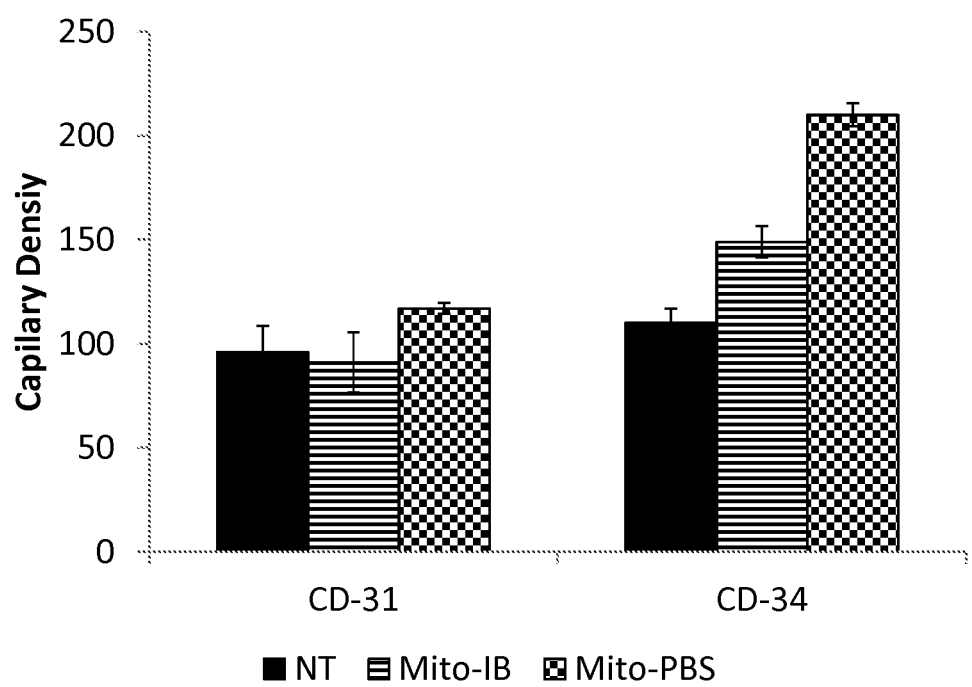
FIG. 16 is a bar graph comparing the density of CD-31 and CD-34 positive capillaries in muscle sections from ischemic mice that were either non-treated (NT) or treated with mitochondria in isolation buffer (Mito-IB) or mitochondria in PBS (Mito-PBS).

Capillary density was measured in each muscle section as the mean number of capillaries relative to the total area comprising blood vessels in the examined section. As can be seen in FIG. 16, sections of muscles treated with mitochondria in IB showed a higher density of CD-34 positive capillaries, relative to sections of muscles from non-treated mice. Sections of muscles treated with mitochondria in PBS showed a higher density of CD-34 positive capillaries, relative to sections treated with mitochondria in IB. As CD 34 is expressed during small capillary formation, the results support capillary formation following treatment with mitochondria.

As can be seen in FIG. 16, the density of CD-31 positive capillaries in sections of muscles treated with mitochondria in PBS was higher than in sections of untreated muscles. However, CD-31 positive capillaries in sections of muscles treated with mitochondria in IB were as dense as the corresponding capillaries in non-treated mice.

Example 17

Figure 17A:
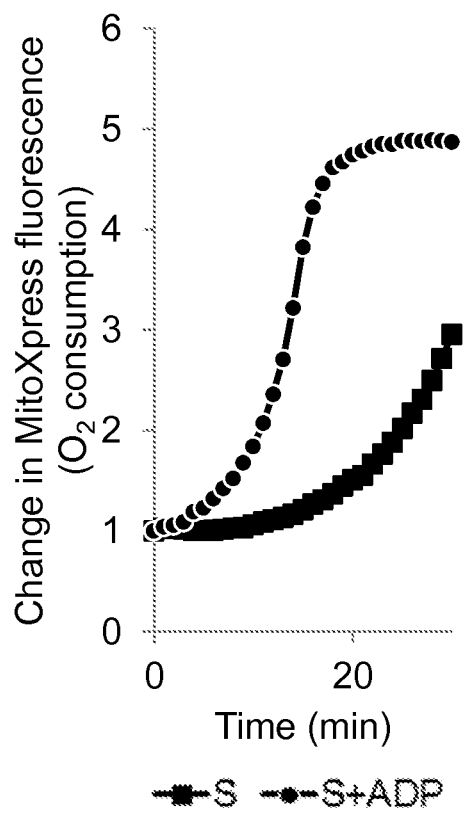
FIGS. 17A-C are dot plots (17A, 17B) comparing the change in oxygen consumption of mitochondria suspended in isolation buffer (17A) and PBS (17B), and a bar graph (17C) comparing citrate synthase release from mitochondria suspended in isolation buffer vs. PBS. S=presence of 25 mM Succinate, S+ADP=presence of 25 mM Succinate and 1.65 mM ADP.
Figure 17B:
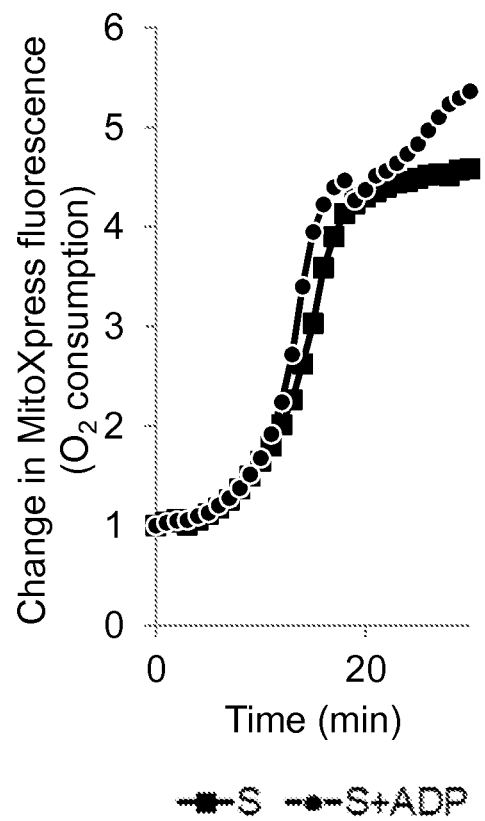

Comparison of Oxygen Consumption and Membrane Integrity of Mitochondria Incubated in Isolation Buffer Vs. Mitochondria Incubated in PBS Mitochondria were isolated from mouse term placenta using isolation buffer (IB) (200 mM Sucrose, 1 mM EGTA/Tris pH 7.4, 10 mM Tris/Mops pH 7.4 supplemented with 0.2% fatty acid free BSA). The mitochondria pellet was either suspended in IB (without BSA) and incubated on ice, or suspended in PBS and incubated at 37° C. for 10 min. Oxygen consumption was measured for 50 μg mitochondria incubated in the presence of succinate (S) or succinate+ADP (S+A) using the MitoXpress fluorescence probe (Luxcel). As can be seen in FIG. 17, mitochondria that have been incubated with PBS (B) show oxygen consumption corresponding to un-coupled mitochondria, while mitochondria incubated in IB (A) show oxygen consumption corresponding to coupled mitochondria.

Figure 17C:
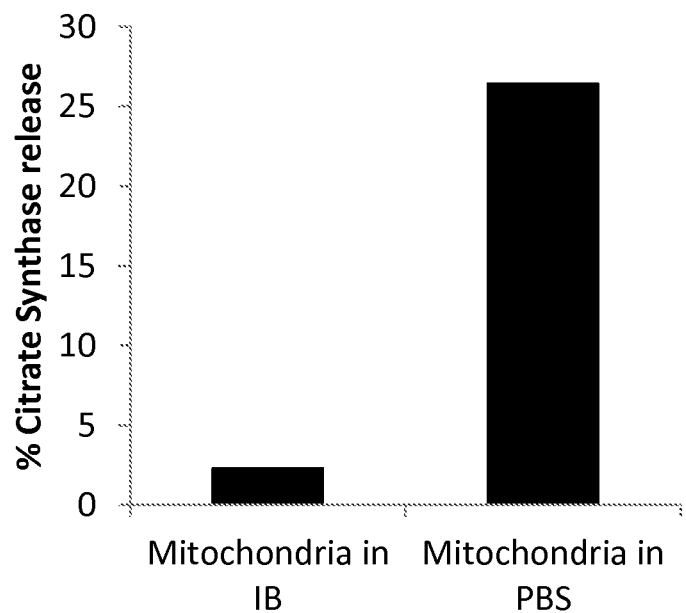

Mitochondrial inner membrane integrity of mitochondria incubated in IB was compared to that of mitochondria incubated in PBS by measuring citrate synthase release using the CS0720 kit (Sigma). FIG. 17C shows that mitochondria that were incubated in PBS have a decreased membrane integrity, as witnessed by citrate synthase release.

Example 18

Comparison of Oxygen Consumption and Membrane Integrity of Mitochondria Incubated in Isolation Buffer Vs. Mitochondria Incubated in Cell Culture Medium Mitochondria were isolated from mouse term placenta using isolation buffer (IB) (200 mM Sucrose, 1 mM EGTA/Tris pH 7.4, 10 mM Tris/Mops pH 7.4 supplemented with 0.2% fatty acid free BSA). The mitochondria pellet was suspended for 1 hour at 37° C. either in IB or OptiMEM medium (Gibco).

Figure 18A:
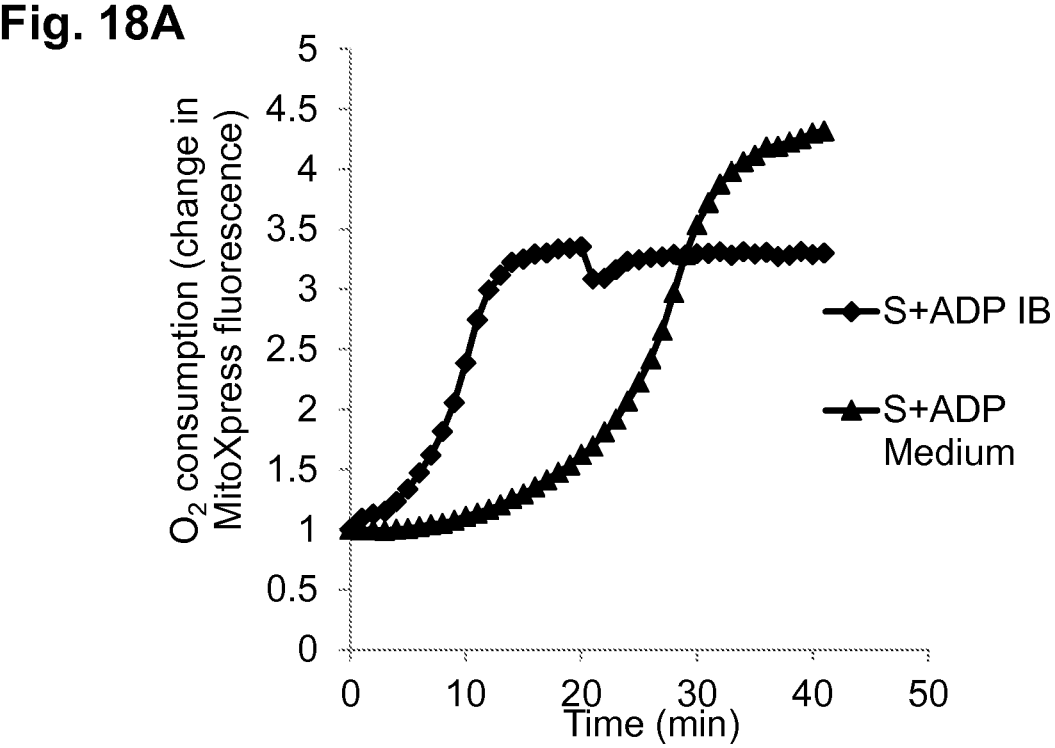
FIGS. 18A-B are a dot plot and bar graph comparing change in oxygen consumption (18A) and citrate synthase release (18B) of mitochondria suspended in isolation buffer vs. Medium.

Oxygen consumption was measured for 50 μg mitochondria incubated in the presence of succinate+ADP (S+A) using the MitoXpress fluorescence probe (Luxcel). FIG. 18A shows that mitochondria that have been incubated in OptiMEM medium show reduced rate of oxygen consumption relative to mitochondria incubated in IB.

Figure 18B:
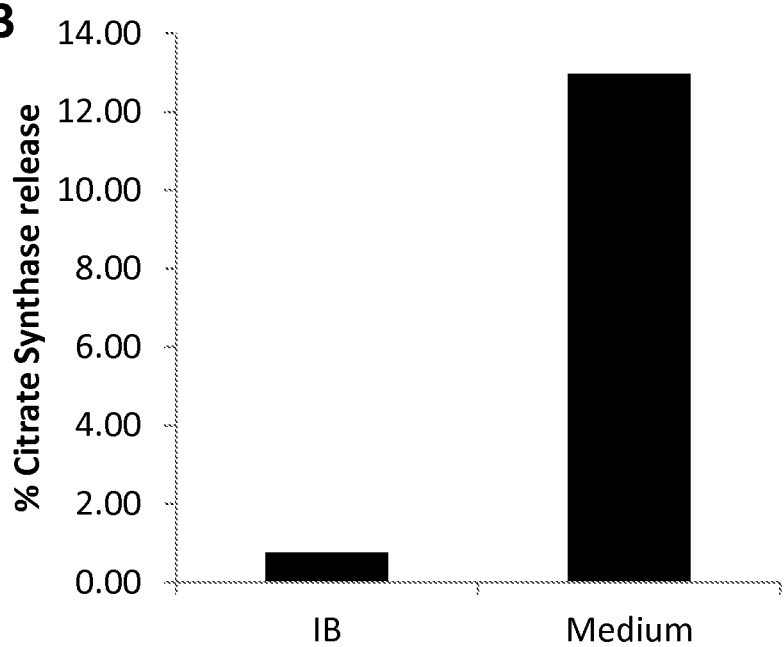

Mitochondrial inner membrane integrity of mitochondria incubated in IB was compared to that of mitochondria incubated in OptiMEM medium by measuring citrate synthase release using the CS0720 kit (Sigma). FIG. 18B shows that mitochondria that were incubated in OptiMEM medium have decreased membrane integrity, as witnessed by citrate synthase release.

Example 19

Citrate Synthase and COX I Activity in Mouse Hind Limb Muscles Treated with Mitochondrial Compositions Mouse hind limb muscle was injected with 100 μl of either isolation buffer or 3.5, 35 or 350 μg of mitochondrial composition (derived from human term placentas according to the method presented in Example 1). Muscles were removed 3 hours following injection, snap-frozen and muscle homogenate was prepared (in a buffer comprising 250 mM sucrose, 2 mM ethylenediaminetetraacetic acid, 10 mM Tris, 50 mg/ml heparin and 10 mg protein/ml Ca).

To assay citrate synthase activity 10-12 μg protein (solubilized in 0.25% triton X-100 for 5 minutes on ice) were incubated 5-7 minutes at 37° C. in a 1 ml solution comprising 100 mM Tris pH=8.1, 1 mM DTNB, 0.3 mM AcetylCoA and 0.5 mM Oxaloacetate. Next, emission was examined under 410 nm To assay COX I activity 1-2 μg protein (solubilized in 0.5 mg/ml sodiumdodecylmaltoside for 5 minutes on ice) were incubated 3-5 minutes at 37° C. in a 1 ml solution comprising 10 mM potassiumphosphate pH=7.0 and 50 μM reduced cytochrome C. Next, emission was examined under 550 nm.

Figure 19:
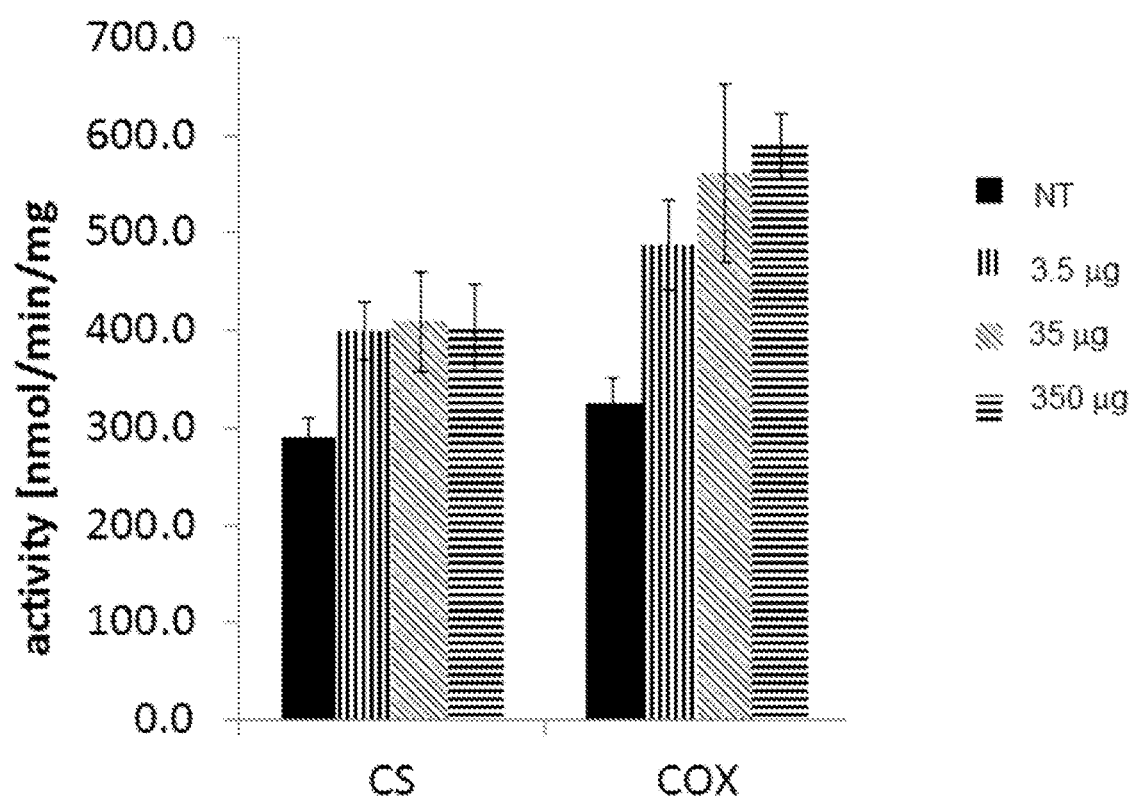
FIG. 19 is a bar graph comparing citrate synthase and COX I activity in mouse hind limb muscles injected with mitochondria isolation buffer (NT) or different doses of mitochondrial composition.

As can be seen in FIG. 19, injection of mitochondrial compositions resulted in an increase in citrate synthase and Cox I activity.

Example 20

Induction of Ex-Vivo Angiogenesis by Mitochondria or Mitochondria-Conditioned Medium The pro-angiogenic potential of mouse term placental mitochondria was assessed in a mouse aortic ring model according to the protocol by Baker M et al (Nature protocols, 2012, 7(1):89-104). Briefly, thoracic aorta were removed from female C57/BL mice and cut into 0.5 mm rings. Next, 0.5 mm thick aortic rings were incubated for 24 hours within OptiMEM buffer (Gibco) with either 12.5 μg/ml mitochondria (M), with a mitochondria conditioned medium (M cond) prepared by incubating 12.5 μg/ml mitochondria in OptiMEM medium for 24 hours in 37° C. and filtering the medium through a 0.2 μm filter, or with mitochondria that are separated from the aortic rings by a 0.4 mm filter (M filter 0.4). The mitochondria used were derived from mouse term placenta.

Figure 20:
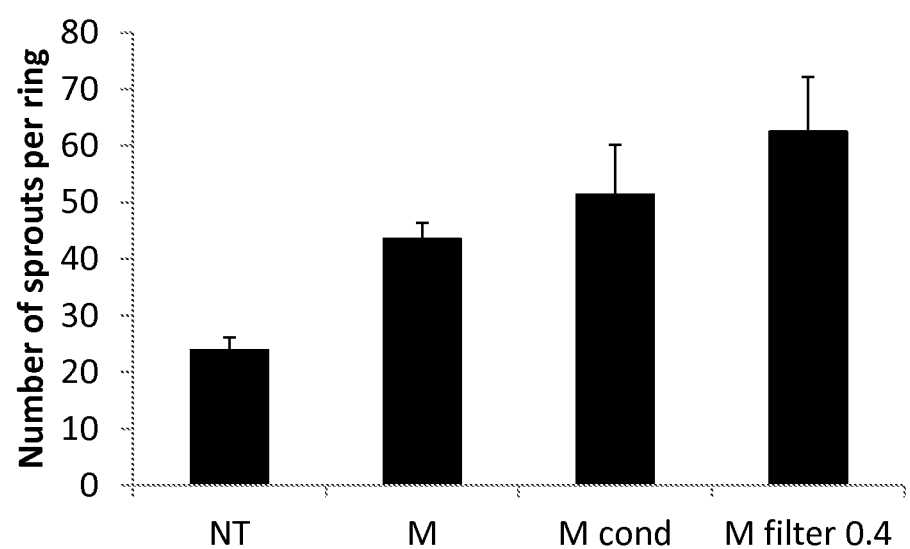
FIG. 20 is a bar graph comparing the number of sprouts from non-treated aortic rings (NT), or aortic rings treated with either mitochondria (M), mitochondria incubated in conditioned media (M Cond) or mitochondria separated from aortic rings using a 0.4 mm filter (M filter 0.4).

After 24 hours the rings were embedded in rat tail collagen matrix, one ring per well in a 96 wells plate, and incubated for 8 days. Next, the number of sprouts per ring were counted. As can be seen in FIG. 20, the mitochondria and conditioned medium induced an increase in the number of sprouts per ring.

Example 21

Oxygen Consumption of Mouse Aortic Rings Treated with Mitochondria

Figure 21:
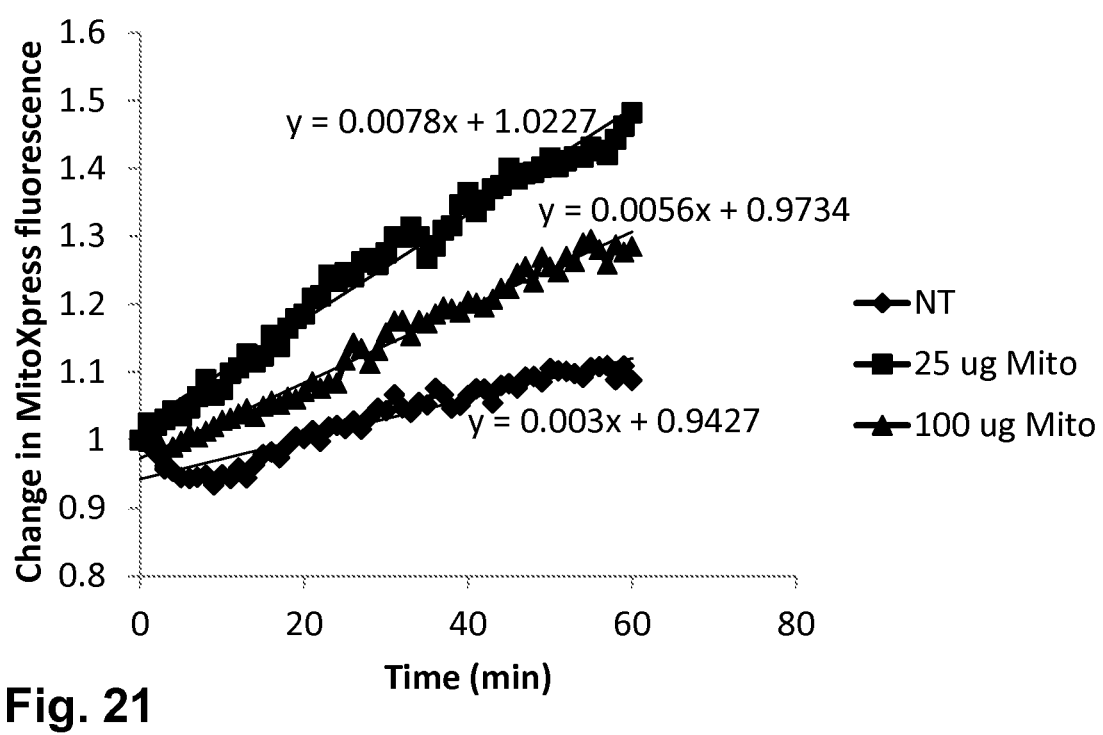
FIG. 21 is a dot plot comparing change in oxygen consumption rate of mouse aortic rings which were untreated (NT) or treated with different concentrations of mitochondria.

Mouse aortic rings were produced as described in Example 19 and incubated within Optimum buffer (Gibco)

for 3 hours with either 12.5 or 50 µg/ml of mouse placental mitochondria. Next, the rings were transferred to black 96-well plates in 150 µl Optimum buffer and 10 µl of Mitoxpress probe (Luxcel), covered with 150 µl mineral oil. To assay oxygen consumption, change in fluorescence (ex/em 380/650 nm) was measured for 1 hour using a Tecan plate reader. As can be seen in FIG. 21, mitochondria induced an increase in oxygen consumption rate of the aortic rings.

Example 22

Oxygen Consumption of Mouse Endothelial Cells Treated with Mitochondria

Mouse endothelial cells (bEND3, ATCC) were seeded in 24 wells at a concentration of 450,000 cells per well. Mitochondria were isolated from mouse term placenta and the cells were incubated for 3 hours with or without 12.5 µg mitochondria/ml medium.

Figure 22:
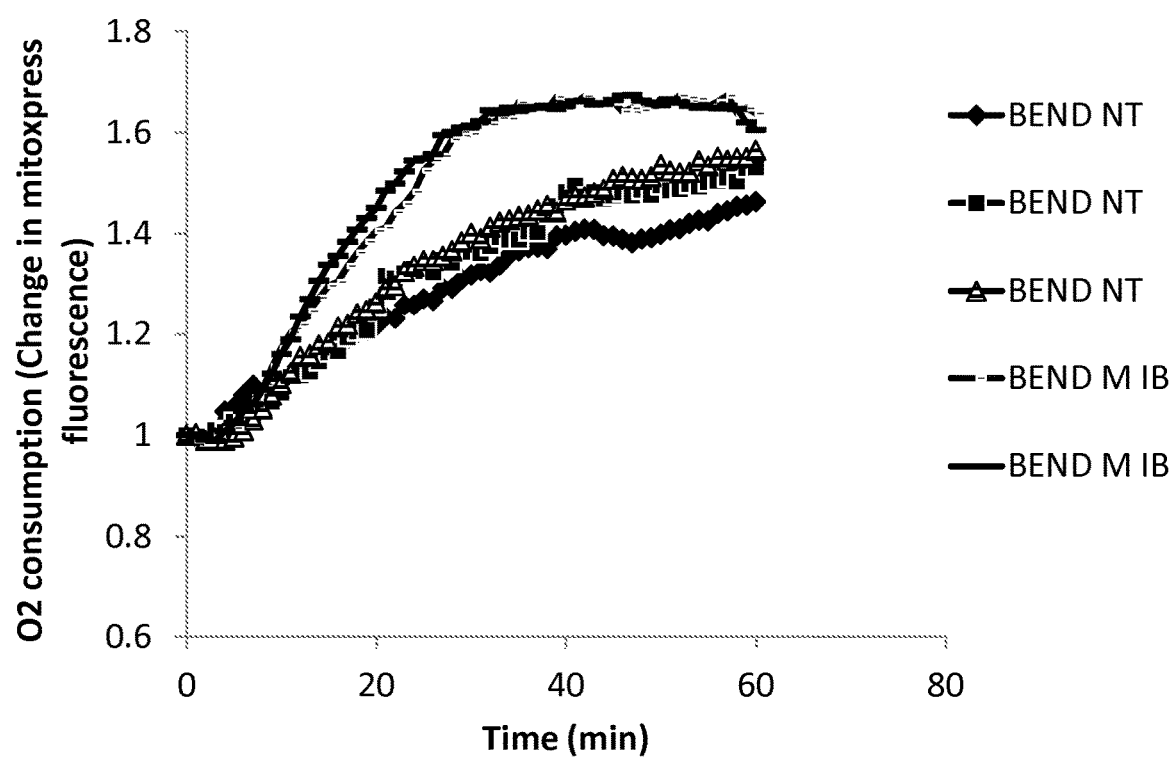
FIG. 22 is a dot plot comparing change in oxygen consumption rate of bEND3 mouse endothelial cells treated with mitochondria isolation buffer (BEND NT) or a mitochondrial composition (BEND M IB).

$O_2$ consumption of the cells was measured using the MitoXpress fluorescence probe (Luxcel) and a Tecan plate reader. The percentage change in fluorescence was calculated relative to the level of fluorescence at time 0. As can be seen in FIG. 22, cells that were treated with mitochondria show increased oxygen consumption.

Example 23

Comparison of Angiogenesis Induced by Human Placental Mitochondria Vs. Human Blood-Cell Mitochondria The femoral arteries of 9 weeks old Blab/c male mice were ligated twice with 6-0 silk thread and transected between the ligatures. The transection wound was closed using a 4-0 silk thread and the mice were allowed to recover. On day 1, 24 hours post-surgery, each animal received an intramuscular injection of either IB, 3.5 µg of human placental mitochondria suspended in IB or 3.5 µg of blood-cell derived mitochondria suspended in IB (200 mM Sucrose, 1 mM EGTA/Tris pH 7.4, 10 mM Tris/Mops pH 7.4). The intramuscular injection was performed at two sites—the proximal and the distal side of the surgical wound. A volume of 50 µl was injected at each location arriving at a total volume of 100 µl.

The human placental mitochondria used in the experiment were obtained according to the method presented in Example 1. The human placental mitochondria were frozen at −70° C. for 6 days and thawed prior to injection.

In order to obtain mitochondria from human blood cells, leukocytes and platelets were isolated as follows:
1. Blood samples from healthy subjects were collected in an EDTA-containing bag.
2. The blood was transferred to 50 ml tubes.
3. The tubed were centrifuged at 1800 g for 15 min at room temperature.
4. The mid layer (Buffy coat) and the supernatant were collected into separate tubes.
5. The supernatant was centrifuged at 14500 g for 20 min
6. The platelet rich pellet was frozen at −70° C. for several minutes, than thawed and re-suspended in IB.
7. Leukocytes were isolated from the Buffy Coat using the Lymphoprep kit (Axis-Shield) according to the manufacturer's procedure.

Next, mitochondria were produced from the isolated platelets and leukocytes according to the following protocol:

1. Pellets of the isolated platelets and leukocytes were pooled, re-suspended in 10 ml IB+0.2% BSA and homogenized using a Teflon-glass homogenizer.
2. The homogenate was centrifuged at 600 g for 10 minutes.
3. The supernatant is kept in a new tube and the pellet is re-homogenized as in step 1.
4. The homogenate was centrifuged at 600 g for 10 minutes.
5. The homogenates of steps 2 and 4 were pooled and passed through a 0.5 µm filter.
6. The homogenate was centrifuged at 7000 g for 15 min at 4° C.
7. Pellets were washed with IB.
8. The homogenate was centrifuged at 7000 g for 15 min at 4° C.
9. The resulting mitochondrial pellet was re-suspended in IB.
10. The mitochondria were frozen at −70° C. for a month and thawed prior to injection.

Figure 23:
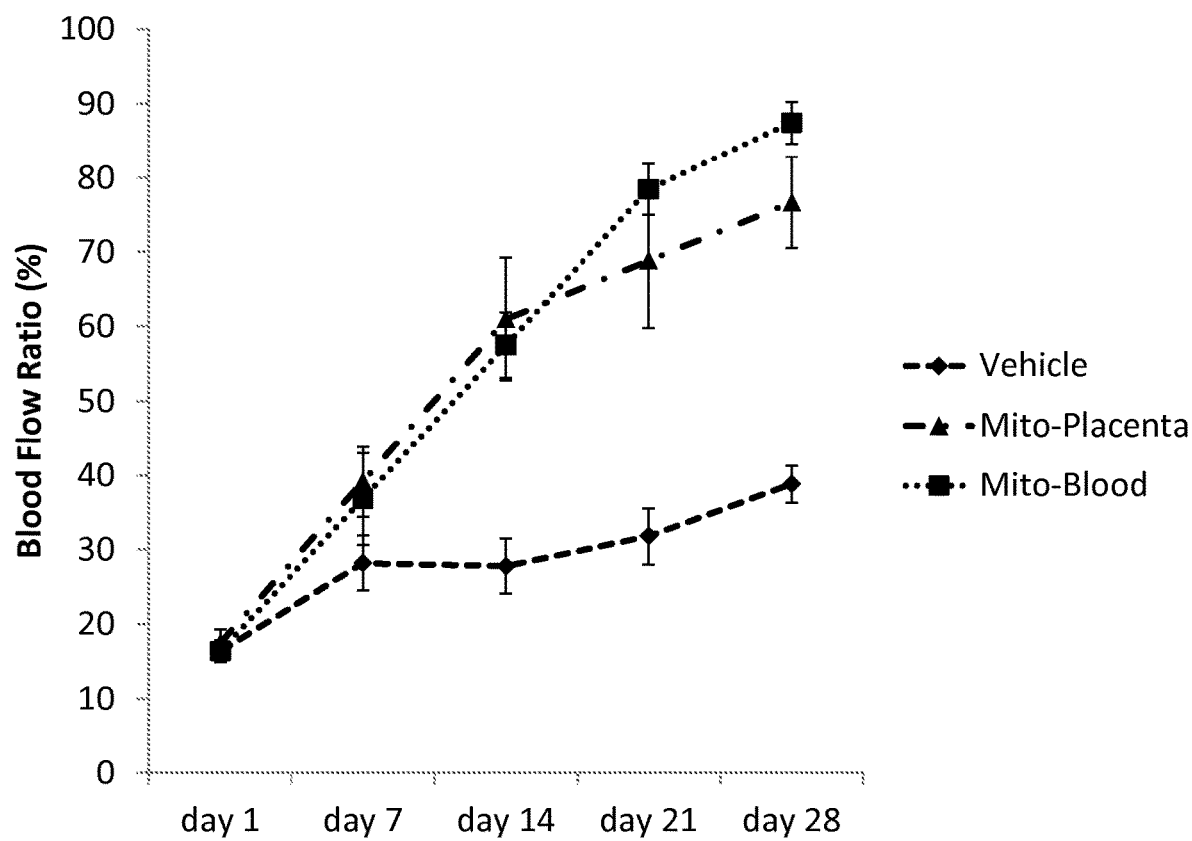
FIG. 23 is a graph comparing blood flow ratios resulting from treatment of mouse hind-limb ischemia with either human placental mitochondria (Mito-Placenta), human mitochondria derived from blood cells (Mito-Blood) or isolation buffer (Vehicle).

Blood flow in hind legs of both sides was measured using a non-contact laser Doppler prior to surgery and on days: 1, 7 14, 21, and 28 post surgery. Blood flow measurements were expressed as the ratio between the flow in the ischemic limb and the intact limb. As can be seen in FIG. 23, both mitochondria derived from human placenta (Mito-Placenta) and mitochondria derived from human blood cells (Mito-Blood) induced an increase in blood flow ratio as compared to treatment with IB (Vehicle), suggesting an angiogenesis-induction ability for mitochondria of both origins.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of inducing angiogenesis in a tissue in vivo comprising:
    thawing a frozen composition, wherein the composition comprises partially purified mitochondria, wherein the mitochondria include intact and ruptured mitochondria; wherein the weight of the partially purified mitochondria constitutes between 20-80% of the combined weight of the composition relative to other sub-cellular fractions in the composition; wherein the mitochondria are at least as functional as control mitochondria that have not undergone a freeze-thaw cycle; wherein the mitochondria are derived from a mammalian cell; and wherein the composition comprises a saccharide; and
    administering to the tissue a therapeutically effective amount of the thawed composition,
    thereby inducing angiogenesis in a tissue as compared with administration of a control vehicle.

2. The method of claim 1, wherein the partially purified mitochondria are derived from a cell or a tissue selected from the group consisting of: human placenta, human placental cell grown in culture and a human blood cell.

3. The method of claim 1, wherein said composition further comprises a hypertonic solution.

4. The method of claim 1, wherein the tissue is selected from the group consisting of: an ischemic tissue, a tissue at risk of being affected with an ischemic damage, a tissue at risk of being affected by a vascular occlusion and a combination thereof.

5. The method of claim 1, wherein said inducing angiogenesis is selected from the group consisting of: enhancing the level of blood perfusion, restoring blood flow, inducing blood flow, inducing growth of new blood vessels from pre-existing vessels, enhancing growth of new blood vessels from preexisting vessels, inducing neovascularization and a combination thereof.

6. The method of claim 1, wherein the tissue is associated with critical limb ischemia.

7. A method for treating a subject afflicted with a pathology which would benefit from angiogenesis comprising:
(a) thawing a frozen composition, wherein the composition comprises partially purified mitochondria, wherein the mitochondria include intact and ruptured mitochondria; wherein the weight of the partially purified mitochondria constitutes between 20-80% of the combined weight of the composition relative to other sub-cellular fractions in the composition; wherein the mitochondria are at least as functional as control mitochondria that have not undergone a freeze-thaw cycle; and wherein the composition comprises a saccharide; and
(b) administering a therapeutically effective amount of the thawed composition to a tissue afflicted with a pathology which would benefit from angiogenesis, thereby treating the subject afflicted with the pathology which would benefit from angiogenesis as compared to a vehicle treated control.

8. The method of claim 7, wherein said pathology which would benefit from angiogenesis is critical limb ischemic.

9. The method of claim 1, wherein the saccharide is sucrose.

10. The method of claim 7, wherein the saccharide is sucrose.

11. The method of claim 1, wherein the saccharide is at concentration of about 20 mM to 200 mM.

12. The method of claim 7, wherein the saccharide is at concentration of about 20 mM to 200 mM.

\* \* \* \* \*